United States Patent
Hoffman et al.

(10) Patent No.: US 11,014,889 B2
(45) Date of Patent: *May 25, 2021

(54) FUNGICIDAL PYRIDYLAMIDINES

(71) Applicant: SYNGENTA PARTICIPATIONS AG, Basel (CH)

(72) Inventors: Thomas James Hoffman, Stein (CH); Sarah Sulzer-Mosse, Stein (CH); Kurt Nebel, Stein (CH); Fredrik Emil Malcolm Cederbaum, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/194,034

(22) Filed: Nov. 16, 2018

(65) Prior Publication Data

US 2019/0084936 A1 Mar. 21, 2019

Related U.S. Application Data

(62) Division of application No. 15/127,911, filed as application No. PCT/EP2015/057088 on Mar. 31, 2015, now Pat. No. 10,173,983.

(30) Foreign Application Priority Data

Apr. 11, 2014 (EP) .................................. 14164464

(51) Int. Cl.
*C07D 213/84* (2006.01)
*C07D 213/74* (2006.01)
*A01N 43/40* (2006.01)

(52) U.S. Cl.
CPC .......... *C07D 213/84* (2013.01); *A01N 43/40* (2013.01); *C07D 213/74* (2013.01)

(58) Field of Classification Search
CPC .................................................... C07D 213/84
USPC ......................................................... 514/344
See application file for complete search history.

(56) References Cited

U.S. PATENT DOCUMENTS 9,326,513 B2 * 5/2016 Haas ..................... A01N 43/40
10,173,983 B2 * 1/2019 Hoffman ............. C07D 213/84

FOREIGN PATENT DOCUMENTS

| WO | 2008/101682 A2 | 8/2008 | |
|---|---|---|---|
| WO | WO 2008101682 * | 8/2008 | .......... C07D 213/84 |
| WO | 2012/146125 A1 | 11/2012 | |

OTHER PUBLICATIONS

Dellavalle, Chilean J of Agricultural Research, 2011,71(2), 231-239.*
International Search Report dated May 20, 2015 for International Patent Application No. PCT/EP2015/057088.

* cited by examiner

*Primary Examiner* — Nizal S Chandrakumar
(74) *Attorney, Agent, or Firm* — Baker & Hostetler LLP; Toni-Junell Herbert

(57) ABSTRACT

The invention relates to compounds of formula (I), wherein $R^1$, $R^2$, $R^3$, $R^4$, $R^5$, and $R^6$ are as defined in the claims. The invention further provides compositions which comprise these compounds and to their use in agriculture or horticulture for controlling or preventing infestation of plants by phytopathogenic microorganisms, preferably fungi.

6 Claims, No Drawings

FUNGICIDAL PYRIDYLAMIDINES

This application is a divisional of U.S. patent application Ser. No. 15/127,911, filed Sep. 21, 2016, which is the national phase of International Application No. PCT/EP2015/057088, filed Mar. 31, 2015, which claims priority to EP 14164464.1 filed Apr. 11, 2014, the contents of all of which are incorporated by reference herein in their entireties.

The present invention relates to novel microbiocidal, in particular fungicidal, pyridylamidine compounds. It further relates to intermediates used in the preparation of these compounds, to compositions which comprise these compounds, and to their use in agriculture or horticulture for controlling or preventing infestation of plants by phytopathogenic microorganisms, preferably fungi.

Certain pyridylamidines derivatives have been proposed in the literature as microbiocidal active ingredients in pesticides. For example, WO 00/46184 and WO 03/093224 disclose pyridylamidines which are useful as fungicides. However, the biological properties of these known compounds are not entirely satisfactory for controlling or preventing infestation of plants by phytopathogenic microorganisms, which is why there is a need to provide other compounds which have microbicidal properties.

The present invention relates to compounds of formula (I)

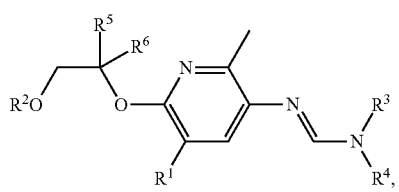

wherein $R^1$ represents hydrogen, halogen, cyano, OH, $NH_2$, $C_1$-$C_4$ alkyl, $C_3$-$C_6$ cycloalkyl, $NH(C_1$-$C_4$ alkyl), $N(C_1$-$C_4$ alkyl)$_2$, $CO(C_1$-$C_4$ alkyl), $CO_2(C_1$-$C_4$ alkyl), $CO_2H$, $CONH(C_1$-$C_4$ alkyl), $CON(C_1$-$C_4$ alkyl)$_2$, $SO_2NH(C_1$-$C_4$ alkyl), $SO_2N(C_1$-$C_4$ alkyl)$_2$, $C_1$-$C_4$ haloalkyl, $C_1$-$C_4$ alkoxy, $C_1$-$C_4$ haloalkoxy, $C_1$-$C_4$ alkyl-$C_1$-$C_4$ alkoxy or $C_2$-$C_4$ alkynyl;

$R^2$ represents $C_3$-$C_6$alkyl, $C_3$-$C_6$alkenyl, $C_3$-$C_6$alkynyl, $R^7$ or —$C_1$-$C_2$alkyl-$R^7$, each of which may be optionally substituted by one or more groups independently selected from the group consisting halogen, $C_1$-$C_4$ alkyl, $C_1$-$C_4$ haloalkyl and $C_1$-$C_4$ haloalkoxy;

$R^3$ and $R^4$ independently of each other represent hydrogen, $C_1$-$C_4$ alkyl or $C_3$-$C_6$ cycloalkyl; or $R^3$ and $R^4$ together with the nitrogen atom to which they are attached form a 3-6-membered saturated cyclic group;

$R^5$ represents H, $C_1$-$C_4$ alkyl or $C_1$-$C_4$ haloalkyl;

$R^6$ represents $C_1$-$C_4$ alkyl, $C_1$-$C_4$ alkoxy, $C_1$-$C_4$ haloalkyl or $C_1$-$C_4$ haloalkoxy;

$R^7$ represents a three- to ten-membered monocyclic or fused bicyclic ring system which can be aromatic, partially saturated or fully saturated and can contain 1 to 4 hetero atoms selected from the group consisting of nitrogen, oxygen and sulfur, it being possible for the three- to ten-membered ring system itself to be optionally substituted by one or more groups independently selected from the group consisting halogen, $C_1$-$C_4$ haloalkyl, $C_1$-$C_4$ alkoxy and $C_1$-$C_4$ haloalkoxy;

and tautomers/isomers/enantiomers/salts and N-oxides of these compounds

Substituents at a nitrogen atom are always different from halogen. A hydroxy, mercapto or amino substituent is not to be placed on an α-carbon relative to a heteroatom of a core fragment.

Halogen, either as a lone substituent or in combination with another substituent (e.g. haloalkyl) is generally fluorine, chlorine, bromine or iodine, and usually fluorine, chlorine or bromine.

Each alkyl moiety (including the alkyl moiety of alkoxy, alkylthio, etc.) is a straight or branched chain and, depending on the number of carbon atoms it contains, is, for example, methyl, ethyl, n-propyl, n-butyl, n-pentyl, n-hexyl, isopropyl, sec-butyl, iso-butyl, tert-butyl, neo-pentyl, n-heptyl or 1,3-dimethylbutyl, and usually methyl or ethyl.

The alkenyl and alkynyl groups can be mono- or di-unsaturated and examples thereof are derived from the above mentioned alkyl groups.

The alkenyl group is an unsaturated straight or branched chain having a carbon-carbon double bond and, depending on the number of carbon atoms it contains, is, for example ethenyl, 1-propenyl, 2-propenyl, 1-methyl-ethenyl, 1-butenyl, 2-butenyl, 3-butenyl, 1-methyl-1-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, and usually 2-propenyl, 1-methyl-2-propenyl, 2-butenyl, 2-methyl-2-propenyl.

The alkynyl group is an unsaturated straight or branched chain having a carbon-carbon triple bond and, depending on the number of carbon atoms it contains, is, for example ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 3,3,-dimethyl-1-butynyl, 1-ethyl-2-butynyl, 1,1-dimethyl-2-butynyl, 1-ethyl-3-butynyl, 2-ethyl-3-butynyl, 1,1-dimethyl-3-butynyl, 2,2-dimethyl-3-butynyl, 1,2-dimethyl-3-butynyl.

Haloalkyl moieties are alkyl moieties which are substituted by one or more of the same or different halogen atoms and are, for example, monofluoromethyl, difluoromethyl, trifluoromethyl, monochloromethyl, dichloromethyl, trichloromethyl, 2,2,2-trifluoroethyl, 2,2-difluoroethyl, 2-fluoroethyl, 1,1-difluoroethyl, 1-fluoroethyl, 2-chloroethyl, pentafluoroethyl, 1,1-difluoro-2,2,2-trichloroethyl, 2,2,3,3-tetrafluoroethyl and 2,2,2-trichloroethyl, and typically trichloromethyl, difluorochloromethyl, difluoromethyl, trifluoromethyl and dichlorofluoromethyl.

Alkoxy is, for example, methoxy, ethoxy, propoxy, iso-propoxy, n-butoxy, iso-butoxy, sec-butoxy and tert-butoxy, and usually methoxy or ethoxy.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy, and usually difluoromethoxy, 2-chloroethoxy and trifluoromethoxy.

Alkylthio is, for example, methylthio, ethylthio, propylthio, iso-propylthio, n-butylthio, iso-butylthio, sec-butylthio or tert-butylthio, and usually methylthio or ethylthio.

Alkylsulphonyl is, for example, methylsulphonyl, ethylsulphonyl, propylsulphonyl, iso-propylsulphonyl, n-butylsulphonyl, iso-butylsulphonyl, sec-butylsulphonyl or tert-butylsulphonyl, and usually methylsulphonyl or ethylsulphonyl.

Alkylsulphinyl is, for example, methylsulphinyl, ethylsulphinyl, propylsulphinyl, iso-propylsulphinyl, n-butylsulphinyl, iso-butylsulphinyl, sec-butylsulphinyl or tert-butylsulphinyl, and usually methylsulphinyl or ethylsulphinyl.

Cycloalkyl may be saturated or partially unsaturated, preferably fully saturated, and is, for example, cyclopropyl, cyclobutyl, cyclopentyl or cyclohexyl.

Alkoxyalkyl is, for example, methoxymethyl, methoxyethyl, ethoxymethyl, ethoxyethyl, n-propoxymethyl, n-propoxyethyl, iso-propoxymethyl or iso-propoxyethyl.

Aryl includes phenyl, naphthyl, anthracyl, fluorenyl and indanyl, but is usually phenyl.

Carbocycle includes cycloalkyl groups and aryl groups.

Heterocycloalkyl is a non-aromatic ring that may be saturated or partially unsaturated, preferably fully saturated, containing carbon atoms as ring members and at least one heteroatom selected from O, S and N as ring members. Examples include oxiranyl, oxetanyl, tetrahydrofuranyl, tetrahydropyranyl, 1,3-dioxolanyl, 1,4-dioxanyl, aziridinyl, azetidinyl, pyrrolidinyl, piperidinyl, oxazinanyl, morpholinyl, thiomorpholinyl, imidazolidinyl, pyrazolidinyl and piperazinyl, preferably morpholinyl, pyrrolidinyl, piperdinyl and piperazinyl, more preferably morpholinyl and pyrollidinyl.

Heteroaryl is, for example, a monovalent monocyclic or bicyclic aromatic hydrocarbon radical. Examples of monocyclic groups include pyridyl, pyridazinyl, pyrimidinyl, pyrazinyl, pyrrolyl, pyrazolyl, imidazolyl, triazolyl, tetrazolyl, furanyl, thiophenyl, oxazolyl, isoxazolyl, oxadiazolyl, thiazolyl, isothiazolyl, and thiadiazolyl. Examples of bicyclic groups include quinolinyl, cinnolinyl, quinoxalinyl, benzimidazolyl, benzothiophenyl, and benzothiadiazolyl. Monocyclic heteroaryl groups are preferred, preferably pyridyl, pyrrolyl, imidazolyl and triazolyl, e.g. 1,2,4 triazolyl, pyridyl and imidazolyl being most preferred.

The terms "heterocycle" and "heterocyclic ring" are used interchangeably and are defined to include heterocycloalkyl and heteroaryl groups. Any reference herein to a heterocycle or heterocyclic ring preferably refers to the specific examples given under the definition of heteroaryl and heterocycloalkyl above, and are preferably morpholinyl, pyrrolidinyl, piperdinyl, piperazinyl pyridyl, pyrrolyl, imidazolyl and triazolyl, e.g. 1,2,4 triazolyl, more preferably morpholinyl, pyrollidinyl, pyridyl and imidazolyl. No heterocycle contains adjacent oxygen atoms, adjacent sulphur atoms, or adjacent oxygen and sulphur atoms.

Where a moiety is indicated as being (optionally) substituted, e.g. alkyl, this includes those moieties where they are part of a larger group, e.g. the alkyl in the alkylthio group. The same applies, e.g. to the phenyl moiety in phenylthio etc. Where a moiety is indicated as being optionally substituted by one or more other groups, preferably there are one to five optional substituents, more preferably one to three optional substituents. Where a moiety is substituted by a cyclic group, e.g. aryl, heteroaryl, cycloalkyl, preferably there are no more than two such substituents, more preferably no more than one such substituent.

The following list provides definitions, including preferred definitions, for substituents $R^1$, $R^2$, $R^3$, $R^4$, $R^5$, $R^6$ and $R^7$ with reference to compounds of formula I. For any one of these substituents, any of the definitions given below may be combined with any definition of any other substituent given below or elsewhere in this document.

$R^1$ represents hydrogen, halogen, cyano, OH, $NH_2$, $C_1$-$C_4$ alkyl, $C_3$-$C_6$ cycloalkyl, $NH(C_1$-$C_4$ alkyl), $N(C_1$-$C_4$ alkyl)$_2$, $CO(C_1$-$C_4$ alkyl), $CO_2(C_1$-$C_4$ alkyl), $CO_2H$, $CONH(C_1$-$C_4$ alkyl), $CON(C_1$-$C_4$ alkyl)$_2$, $SO_2NH(C_1$-$C_4$ alkyl), $SO_2N(C_1$-$C_4$ alkyl)$_2$, $C_1$-$C_4$ haloalkyl, $C_1$-$C_4$ alkoxy, $C_1$-$C_4$ haloalkoxy, $C_1$-$C_4$ alkyl-$C_1$-$C_4$ alkoxy or $C_2$-$C_4$ alkynyl Preferably, $R^1$ represents hydrogen, halogen, cyano, OH, $NH_2$, $C_1$-$C_4$ alkyl, $C_3$-$C_6$ cycloalkyl, $NH(C_1$-$C_4$ alkyl), $N(C_1$-$C_4$ alkyl)$_2$, $CO(C_1$-$C_4$ alkyl), $CO_2(C_1$-$C_4$ alkyl), $CO_2H$, $CONH(C_1$-$C_4$ alkyl), $CON(C_1$-$C_4$ alkyl)$_2$, $SO_2NH(C_1$-$C_4$ alkyl), $SO_2N(C_1$-$C_4$ alkyl)$_2$, $C_1$-$C_4$ haloalkyl, $C_1$-$C_4$ alkoxy, $C_1$-$C_4$ haloalkoxy, or $C_2$-$C_4$ alkynyl.

More preferably, $R^1$ represents hydrogen, halogen, cyano, OH, $NH_2$, methyl, ethyl, cyclopropyl, $NH(C_1$-$C_2$ alkyl), $N(C_1$-$C_2$ alkyl)$_2$, $CO(C_1$-$C_2$ alkyl), $CO_2(C_1$-$C_2$ alkyl), $CO_2H$, $CONH(C_1$-$C_2$ alkyl), $CON(C_1$-$C_2$ alkyl)$_2$, $SO_2NH(C_1$-$C_2$ alkyl), $SO_2N(C_1$-$C_2$ alkyl)$_2$, $C_1$-$C_4$ fluoroalkyl, $C_1$-$C_4$ alkoxy, $C_1$-$C_2$ haloalkoxy or $C_2$-$C_4$ alkynyl.

Even more preferably, $R^1$ represents hydrogen, halogen, cyano, OH, $NH_2$, methyl, ethyl, cyclopropyl, NHMe, $NMe_2$, COMe, $CO_2Me$, $CO_2H$, CONHMe, $CONMe_2$, $SO_2NHMe$, $SO_2NMe_2$, $CHF_2$, $CF_3$, OMe, $OCHF_2$ or acetylenyl.

Yet more preferably, $R_1$ represents hydrogen, halogen, cyano, methyl, ethyl, cyclopropyl, $CHF_2$, $CF_3$, OMe, or $OCHF_2$.

Most preferably, $R^1$ represents hydrogen, Cl, Br, methyl, $CHF_2$ or cyano.

$R^2$ represents $C_3$-$C_6$alkyl, $C_3$-$C_6$alkenyl, $C_3$-$C_6$alkynyl, $R^7$ or —$C_1$-$C_2$alkyl-$R^7$, each of which may be optionally substituted by one or more groups independently selected from the group consisting halogen, $C_1$-$C_4$ alkyl, $C_1$-$C_4$haloalkyl and $C_1$-$C_4$ haloalkoxy.

Preferably, $R^2$ represents $C_3$-$C_6$alkyl, $C_3$-$C_6$alkenyl, $C_3$-$C_6$alkynyl, $C_3$-$C_6$cycloalkyl, $C_3$-$C_5$cycloalkenyl, —$C_1$-$C_2$alkyl-$C_3$-$C_6$cycloalkyl, —$C_1$-$C_2$alkyl-$C_3$-$C_6$cycloalkenyl, each of which may be optionally substituted by one or more groups independently selected from the group consisting halogen, $C_1$-$C_2$ alkyl, $C_1$-$C_2$ haloalkyl and $C_1$-$C_2$ haloalkoxy.

More preferably, $R^2$ represents $C_3$-$C_6$alkyl, $C_3$-$C_6$alkenyl, $C_3$-$C_6$alkynyl, $C_3$-$C_6$cycloalkyl, $C_3$-$C_5$cycloalkenyl, —$C_1$-$C_2$alkyl-$C_3$-$C_6$cycloalkyl, —$C_1$-$C_2$alkyl-$C_3$-$C_6$cycloalkenyl which may be optionally substituted by one or more groups independently selected from the group consisting fluoro, $C_1$-$C_2$alkyl, $C_1$-$C_2$fluoroalkyl and $C_1$-$C_2$fluoroalkoxy.

Yet more preferably, $R^2$ is n-propyl, iso-propyl, n-butyl, iso-butyl, sec-butyl, tert-butyl, n-pentyl, 2-methylbutyl, 2,2-dimethylpropyl, 2-methylpentyl, 3-methylpentyl, 2,3-dimethylbutyl, 2,2-dimethylbutyl, cyclopropyl, cyclobutyl, cyclopentyl, cyclopentenyl —$CH_2$-cyclopropyl, —$CH_2$-cyclobutyl, —$CH_2$-cyclopentyl, and —$CH_2$-cyclopentenyl, each of which may be optionally substituted by one or more groups independently selected from the group consisting fluoro, methyl and difluoromethoxy.

Yet more preferably again, R₂ is n-propyl, iso-propyl, n-butyl, iso-butyl, sec-butyl, each of which may be optionally substituted by one or more groups independently selected from the group consisting fluoro and difluoromethoxy.

Most preferably, R₂ is n-propyl, iso-propyl, n-butyl, iso-butyl, sec-butyl or cyclopropyl.

In another group of compounds, R² represents C₃-C₆alkyl, C₃-C₆alkenyl, C₃-C₆alkynyl, R⁷ or —C₁-C₂alkyl-R⁷, each of which may be optionally substituted by one or more groups independently selected from the group consisting halogen, C₁-C₄ alkyl and C₁-C₄ haloalkyl.

Preferably in this group of compounds, R² represents C₃-C₆alkyl, C₃-C₆alkenyl, C₃-C₆alkynyl, C₃-C₆cycloalkyl, C₃-C₆cycloalkenyl, —C₁-C₂alkyl-C₃-C₆cycloalkyl, —C₁-C₂alkyl-C₃-C₆cycloalkenyl, each of which may be optionally substituted by one or more groups independently selected from the group consisting halogen, C₁-C₂ alkyl and C₁-C₂ haloalkyl.

More preferably in this group of compounds, R² represents C₃-C₆alkyl, C₃-C₆alkenyl, C₃-C₆alkynyl, C₃-C₆cycloalkyl, C₃-C₅cycloalkenyl, —C₁-C₂alkyl-C₃-C₆cycloalkyl, —C₁-C₂alkyl-C₃-C₆cycloalkenyl which may be optionally substituted by one or more groups independently selected from the group consisting fluoro, C₁-C₂alkyl and C₁-C₂fluoroalkyl.

Yet more preferably in this group of compounds, R² is n-propyl, iso-propyl, n-butyl, iso-butyl, sec-butyl, tert-butyl, n-pentyl, 2-methylbutyl, 2,2-dimethylpropyl, 2-methylpentyl, 3-methylpentyl, 2,3-dimethylbutyl, 2,2-dimethylbutyl, cyclopropyl, cyclobutyl, cyclopentyl, cyclopentenyl —CH₂-cyclopropyl, —CH₂-cyclobutyl, —CH₂-cyclopentyl, and —CH₂-cyclopentenyl, each of which may be optionally substituted by one or more groups independently selected from the group consisting fluoro and methyl.

Yet more preferably again in this group of compounds, R₂ is n-propyl, iso-propyl, n-butyl, iso-butyl, sec-butyl, each of which may be optionally substituted by one or more fluoro.

R³ and R⁴ independently of each other represent hydrogen, C₁-C₄ alkyl or C₃-C₆ cycloalkyl; or R³ and R⁴ together with the nitrogen atom to which they are attached form a 3-6-membered saturated cyclic group;

Preferably, R³ and R⁴ independently of each other represent hydrogen, C₁-C₃ alkyl or C₃-C₅ cycloalkyl; or R³ and R⁴ together with the nitrogen atom to which they are attached form a 4- or 5-membered saturated cyclic group.

More preferably, R³ and R⁴ independently of each other represent hydrogen, methyl, ethyl, isopropyl or cyclopropyl; or R³ and R⁴ together with the nitrogen atom to which they are attached form a 4-membered saturated cyclic group.

In one group of compounds, R³ is hydrogen or methyl; R⁴ is methyl or ethyl.

Preferably in this group of compounds, R³ represents hydrogen or methyl; R⁴ is ethyl.

R⁵ represents H, C₁-C₄ alkyl or C₁-C₄ haloalkyl.
Preferably, R⁵ represents H or C₁-C₄ alkyl.
More preferably, R⁵ represents H or methyl
Most preferably, R⁵ is hydrogen.

R⁶ represents C₁-C₄ alkyl, C₁-C₄ alkoxy, C₁-C₄ haloalkyl or C₁-C₄ haloalkoxy.
Preferably, R⁶ represents C₁-C₄ alkyl or C₁-C₄ alkoxy.
More preferably, R⁶ represents methyl, ethyl, n-propyl, iso-propyl, cyclopropyl, cyclobutyl, cyclopentyl, methoxy or ethoxy.

Even more preferably, R⁶ represents methyl, ethyl, n-propyl, iso-propyl, cyclopropyl, cyclobutyl, or cyclopentyl.

Yet more preferably, R⁶ represents methyl, ethyl, n-propyl, iso-propyl, cyclopropyl, cyclobutyl or cyclopentyl.

Even yet more preferably, R⁶ represents methyl, ethyl, n-propyl, iso-propyl, or cyclopropyl.

More preferably still, R⁶ represents methyl, ethyl, n-propyl or iso-propyl.

Most preferably, R⁶ is methyl.

When R⁵ and R⁶ are not the same, the compounds of formula (I) can occur in (at least) two enantiomeric forms: (Ia) and (Ib).

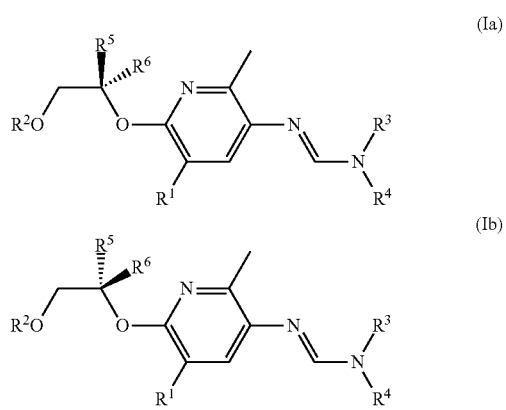

A racemic compound (I) is a 1:1 mixture of the compounds of formula (Ia) and (Ib). Other ratios of (Ia) and (Ib) are possible and part of the present invention. Examples of such ratios of (Ia) to (Ib) are 1:99, 2:98, 5:95, 10:90, 20:80, 30:70; 40:60, 45:55; 55:45; 60;40, 70:30, 80:20, 90:10, 95:5, 98;2, and 99:1.

In one embodiment of the invention, the weight ratio of (Ib) to (Ia) is weighted towards compound of formula (Ia), for example, the ratio of (Ib) to (Ia) being 1:99, 2:98, 5:95, 10:90, 20:80, 30:70; 40:60 or 45:55. More preferably in this embodiment of the invention, the compound of formula (I) consists essentially of the compound of formula (Ia); even more preferably, the compound of formula (I) is the compound of formula (Ia).

In another embodiment of the invention, the weight ratio of (Ia) to (Ib) is weighted towards compound of formula (Ib), for example, the ratio of (Ia) to (Ib) being 1:99, 2:98, 5:95, 10:90, 20:80, 30:70; 40:60 or 45:55. More preferably in this embodiment of the invention, the compound of formula (I) consists essentially of the compound of formula (Ib); even more preferably, the compound of formula (I) is the compound of formula (Ib).

R⁷ represents a three- to ten-membered monocyclic or fused bicyclic ring system which can be aromatic, partially saturated or fully saturated and can contain 1 to 4 hetero atoms selected from the group consisting of nitrogen, oxygen and sulfur, it being possible for the three- to ten-membered ring system itself to be optionally substituted by one or more groups independently selected from the group consisting halogen, C₁-C₄ haloalkyl, C₁-C₄ alkoxy and C₁-C₄ haloalkoxy.

Preferably, R⁷ represents C₃-C₆cycloalkyl, C₃-C₅cycloalkenyl, phenyl, naphthyl, anthracyl, fluorenyl, indanyl, oxiranyl, oxetanyl, tetrahydrofuranyl, tetrahydropyranyl, 1,3-dioxolanyl, 1,4-dioxanyl, aziridinyl, azetidinyl, pyrrolidinyl, piperidinyl, oxazinanyl, morpholinyl, thiomorpholinyl, imidazolidinyl, pyrazolidinyl, piperazinyl, pyridyl, pyridazinyl, pyrimidinyl, pyrazinyl, pyrrolyl, pyrazolyl, imidazolyl, triazolyl, tetrazolyl, furanyl, thiophenyl, oxazolyl, isoxazolyl, oxadiazolyl, thiazolyl, isothiazolyl, thiadiazolyl, quinolinyl, cinnolinyl, quinoxalinyl, benzimidazolyl, benzothiophenyl, or benzothiadiazolyl, each of which is optionally substituted by one or more groups independently selected from the group consisting halogen, $C_1$-$C_4$ haloalkyl, $C_1$-$C_4$alkoxy and $C_1$-$C_4$ haloalkoxy.

More preferably, $R^7$ represents $C_3$-$C_6$cycloalkyl, $C_3$-$C_5$cycloalkenyl, phenyl, naphthyl, anthracyl, fluorenyl, indanyl, morpholinyl, pyrrolidinyl, piperidinyl, piperazinyl, pyridyl, pyrrolyl, imidazolyl and triazolyl, each of which is optionally substituted by one or more groups independently selected from the group consisting halogen, $C_1$-$C_4$haloalkyl, $C_1$-$C_4$ alkoxy and $C_1$-$C_4$ haloalkoxy.

Yet more preferably, $R^7$ represents $C_3$-$C_6$cycloalkyl, $C_3$-$C_5$cycloalkenyl, phenyl, naphthyl, morpholinyl, pyrrolidinyl, piperidinyl, piperazinyl, pyridyl, pyrrolyl, imidazolyl and triazolyl, each of which is optionally substituted by one or more groups independently selected from the group consisting halogen, $C_1$-$C_4$haloalkyl, $C_1$-$C_4$alkoxy and $C_1$-$C_4$ haloalkoxy.

Even more preferably, $R^7$ represents $C_3$-$C_6$cycloalkyl, $C_3$-$C_5$cycloalkenyl, phenyl, morpholinyl, pyrrolidinyl, piperdinyl, piperazinyl, pyridyl, pyrrolyl, imidazolyl and triazolyl, each of which is optionally substituted by one or more groups independently selected from the group consisting halogen, $C_1$-$C_4$ haloalkyl, $C_1$-$C_4$alkoxy and $C_1$-$C_4$ haloalkoxy.

More preferably again, $R^7$ represents $C_3$-$C_6$cycloalkyl, $C_3$-$C_5$cycloalkenyl, phenyl, morpholinyl, pyrollidinyl, pyridyl and imidazolyl, each of which is optionally substituted by one or more groups independently selected from the group consisting halogen, $C_1$-$C_4$ haloalkyl, $C_1$-$C_4$ alkoxy and $C_1$-$C_4$ haloalkoxy.

Most preferably, $R^7$ represents $C_3$-$C_6$cycloalkyl or $C_3$-$C_5$cycloalkenyl, each of which is optionally substituted by one or more groups independently selected from the group consisting halogen, $C_1$-$C_4$ haloalkyl, $C_1$-$C_4$ alkoxy and $C_1$-$C_4$ haloalkoxy In one group of compounds of formula (I), $R^1$ represents hydrogen, halogen, cyano, OH, $NH_2$, $C_1$-$C_4$ alkyl, $C_3$-$C_6$ cycloalkyl, $NH(C_1$-$C_4$ alkyl), $N(C_1$-$C_4$ alkyl$)_2$, $CO(C_1$-$C_4$ alkyl), $CO_2(C_1$-$C_4$ alkyl), $CO_2H$, $CONH(C_1$-$C_4$ alkyl), $CON(C_1$-$C_4$ alkyl$)_2$, $SO_2NH(C_1$-$C_4$ alkyl), $SO_2N(C_1$-$C_4$ alkyl$)_2$, $C_1$-$C_4$ haloalkyl, $C_1$-$C_4$ alkoxy, $C_1$-$C_4$ haloalkoxy, or $C_2$-$C_4$ alkynyl;

$R^2$ represents $C_3$-$C_6$alkyl, $C_3$-$C_6$alkenyl, $C_3$-$C_6$alkynyl, $C_3$-$C_6$cycloalkyl, $C_3$-$C_5$cycloalkenyl, —$C_1$-$C_2$alkyl-$C_3$-$C_6$cycloalkyl, —$C_1$-$C_2$alkyl-$C_3$-$C_6$cycloalkenyl, each of which may be optionally substituted by one or more groups independently selected from the group consisting halogen, $C_1$-$C_4$ haloalkyl and $C_1$-$C_4$ haloalkoxy;

$R^3$ and $R^4$ independently of each other represent hydrogen, $C_1$-$C_4$ alkyl or $C_3$-$C_6$ cycloalkyl; or $R^3$ and $R^4$ together with the nitrogen atom to which they are attached form a 3-6-membered saturated cyclic group;

$R^5$ represents H, $C_1$-$C_4$ alkyl or $C_1$-$C_4$ haloalkyl;

$R^6$ represents $C_1$-$C_4$ alkyl, $C_1$-$C_4$ alkoxy, $C_1$-$C_4$ haloalkyl or $C_1$-$C_4$ haloalkoxy.

In another group of compounds of formula (I), $R^1$ represents hydrogen, halogen, cyano, OH, $NH_2$, methyl, ethyl, cyclopropyl, $NH(C_1$-$C_2$ alkyl), $N(C_1$-$C_2$ alkyl$)_2$, $CO(C_1$-$C_2$ alkyl), $CO_2(C_1$-$C_2$ alkyl), $CO_2H$, $CONH(C_1$-$C_2$ alkyl), $CON(C_1$-$C_2$ alkyl$)_2$, $SO_2NH(C_1$-$C_2$ alkyl), $SO_2N(C_1$-$C_2$ alkyl$)_2$, $C_1$-$C_4$ fluoroalkyl, $C_1$-$C_4$ alkoxy, $C_1$-$C_2$ haloalkoxy or $C_2$-$C_4$ alkynyl;

$R^2$ represents $C_3$-$C_6$alkyl, $C_3$-$C_6$alkenyl, $C_3$-$C_6$alkynyl, $C_3$-$C_6$cycloalkyl, $C_3$-$C_5$cycloalkenyl, —$C_1$-$C_2$alkyl-$C_3$-$C_6$cycloalkyl, —$C_1$-$C_2$alkyl-$C_3$-$C_6$cycloalkenyl, each of which may be optionally substituted by one or more groups independently selected from the group consisting halogen, $C_1$-$C_2$ haloalkyl and $C_1$-$C_2$ haloalkoxy;

$R^3$ and $R^4$ independently of each other represent hydrogen, $C_1$-$C_3$ alkyl or $C_3$-$C_5$ cycloalkyl; or $R^3$ and $R^4$ together with the nitrogen atom to which they are attached form a 5-membered saturated cyclic group;

$R^5$ represents H or $C_1$-$C_4$ alkyl;

$R^6$ represents $C_1$-$C_4$ alkyl, $C_1$-$C_4$ alkoxy, $C_1$-$C_4$ haloalkyl or $C_1$-$C_4$ haloalkoxy.

In another group of compounds of formula (I), $R^1$ represents hydrogen, halogen, cyano, OH, $NH_2$, methyl, ethyl, cyclopropyl, NHMe, $NMe_2$, COMe, $CO_2Me$, $CO_2H$, CONHMe, $CONMe_2$, $SO_2NHMe$, $SO_2NMe_2$, $CHF_2$, $CF_3$, OMe, $OCHF_2$ or acetylenyl;

$R^2$ represents $C_3$-$C_6$alkyl, $C_3$-$C_6$alkenyl, $C_3$-$C_6$alkynyl, $C_3$-$C_6$cycloalkyl, $C_3$-$C_5$cycloalkenyl, —$C_1$-$C_2$alkyl-$C_3$-$C_6$cycloalkyl, —$C_1$-$C_2$alkyl-$C_3$-$C_6$cycloalkenyl which may be optionally substituted by one or more groups independently selected from the group consisting fluoro, $C_1$-$C_2$alkyl, $C_1$-$C_2$fluoroalkyl and $C_1$-$C_2$fluoroalkoxy;

$R^3$ and $R^4$ independently of each other represent hydrogen, methyl, ethyl, isopropyl or cyclopropyl; or $R^3$ and $R^4$ together with the nitrogen atom to which they are attached form a 5-membered saturated cyclic group;

$R^5$ represents H or methyl;

$R^6$ represents $C_1$-$C_4$ alkyl or $C_1$-$C_4$ alkoxy.

In another group of compounds of formula (I), $R_1$ represents hydrogen, halogen, cyano, methyl, ethyl, cyclopropyl, $CHF_2$, $CF_3$, OMe, or $OCHF_2$;

$R_2$ is n-propyl, iso-propyl, n-butyl, iso-butyl, sec-butyl, tert-butyl, n-pentyl, 2-methylbutyl, 2,2-dimethylpropyl, 2-methylpentyl, 3-methylpentyl, 2,3-dimethylbutyl, 2,2-dimethylbutyl, cyclopropyl, cyclobutyl, cyclopentyl, cyclopentenyl-$CH_2$-cyclopropyl, —$CH_2$-cyclobutyl, —$CH_2$-cyclopentyl, and —$CH_2$-cyclopentenyl, each of which may be optionally substituted by one or more groups independently selected from the group consisting fluoro, methyl and difluoromethoxy;

$R^3$ is hydrogen or methyl;

$R^4$ is methyl or ethyl;

$R^5$ represents H or methyl;

$R^6$ represents methyl, ethyl, n-propyl, iso-propyl, cyclopropyl, cyclobutyl, cyclopentyl, methoxy or ethoxy.

In another group of compounds of formula (I), $R^1$ represents hydrogen, Cl, Br, methyl, $CHF_2$ or cyano;

$R_2$ is n-propyl, iso-propyl, n-butyl, iso-butyl, sec-butyl, each of which may be optionally substituted by one or more groups independently selected from the group consisting fluoro and difluoromethoxy;

$R^3$ represents hydrogen or methyl;

$R^4$ is ethyl;

$R^5$ is hydrogen or methyl;

$R^6$ represents methyl, ethyl, n-propyl, iso-propyl, cyclopropyl, cyclobutyl, cyclopentyl, methoxy or ethoxy.

In another group of compounds of formula (I), $R^1$ represents hydrogen, Cl, Br, methyl, $CHF_2$ or cyano;

$R_2$ is n-propyl, iso-propyl, n-butyl, iso-butyl, sec-butyl, each of which may be optionally substituted by one or more groups independently selected from the group consisting fluoro and difluoromethoxy;

$R^3$ represents hydrogen or methyl;
$R^4$ is ethyl;
$R^5$ is hydrogen or methyl;
$R^6$ represents methyl, ethyl, n-propyl, iso-propyl, cyclopropyl, cyclobutyl or cyclopentyl.

In another group of compounds of formula (I), $R^1$ represents hydrogen, Cl, Br, methyl, $CHF_2$ or cyano;
$R_2$ is n-propyl, iso-propyl, n-butyl, iso-butyl, sec-butyl, each of which may be optionally substituted by one or more groups independently selected from the group consisting of fluoro and difluoromethoxy;
$R^3$ represents hydrogen or methyl;
$R^4$ is ethyl;
$R^5$ is hydrogen or methyl;
$R^6$ represents methyl, ethyl, n-propyl or iso-propyl.

In another group of compounds of formula (I), $R^1$ represents hydrogen, Cl, Br, methyl, $CHF_2$ or cyano;
$R_2$ is n-propyl, iso-propyl, n-butyl, iso-butyl, sec-butyl, each of which may be optionally substituted by one or more groups independently selected from the group consisting of fluoro and difluoromethoxy;
$R^3$ represents hydrogen or methyl;
$R^4$ is ethyl;
$R^5$ is hydrogen or methyl;
$R^6$ is methyl.

In another group of compounds of formula (I), $R^1$ represents hydrogen, Cl, Br, methyl, $CHF_2$ or cyano;
$R_2$ is n-propyl, iso-propyl, n-butyl, iso-butyl, sec-butyl or cyclopropyl;
$R^3$ represents hydrogen or methyl;
$R^4$ is ethyl;
$R^5$ is hydrogen;
$R^6$ is methyl.

Tables 1 to 22: Compounds of Formula (I)

The invention is further illustrated by making available the following individual compounds of formula (I) listed below in Tables 1 to 22.

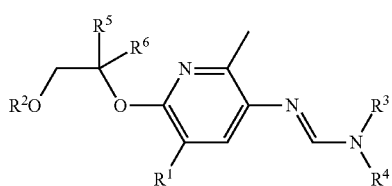

Each of Tables 1 to 22, which follow Table A below, make available 47 compounds of the formula (I) in which $R^2$, $R^3$, $R^4$, $R^5$ and $R^6$ are the substituents defined in Table A and $R^1$ is the substituent defined in the relevant Table 1 to 22. Thus Table 1 individualises 47 compounds of formula (I) wherein for each row of Table A, $R^1$ is as defined in Table 1. Similarly, Table 2 individualises 47 compounds of formula (I) wherein for each row of Table A, $R^1$ is as defined in Table 2; and so on for Tables 3 to 22.

Table A discloses 47 sets of meanings of the variables $R^2$, $R^3$, $R^4$, $R^5$ and $R^6$ in a compound of formula I.

Tables 23 to 44: Compounds of Formula (Ia)

The invention is further illustrated by making available the following individual compounds of formula (Ia) listed below in Tables 23 to 44.

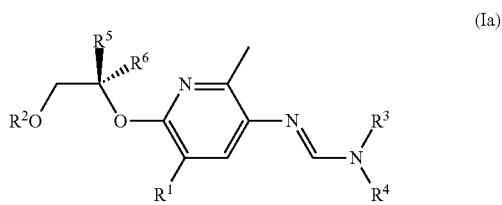

Each of Tables 23 to 44, which follow Table A below, make available 47 compounds of the formula (Ia) in which $R^2$, $R^3$, $R^4$, $R^5$ and $R^6$ are the substituents defined in Table A and $R^1$ is the substituent defined in the relevant Table 23 to 44. Thus Table 23 individualises 47 compounds of formula (Ia) wherein for each row of Table A, $R^1$ is as defined in Table 23. Similarly, Table 24 individualises 47 compounds of formula (Ia) wherein for each row of Table A, $R^1$ is as defined in Table 24; and so on for Tables 25 to 44.

Table A discloses 47 sets of meanings of the variables $R^2$, $R^3$, $R^4$, $R^5$ and $R^6$ in a compound of formula Ia.

Tables 45 to 66: Compounds of Formula (Ib)

The invention is further illustrated by making available the following individual compounds of formula (Ib) listed below in Tables 45 to 66.

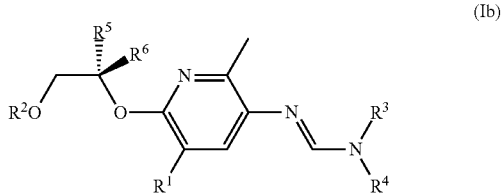

Each of Tables 45 to 66, which follow Table A below, make available 47 compounds of the formula (Ib) in which $R^2$, $R^3$, $R^4$, $R^5$ and $R^6$ are the substituents defined in Table A and $R^1$ is the substituent defined in the relevant Table 45 to 66. Thus Table 45 individualises 47 compounds of formula (Ib) wherein for each row of Table A, $R^1$ is as defined in Table 45. Similarly, Table 46 individualises 47 compounds of formula (Ib) wherein for each row of Table A, $R^1$ is as defined in Table 46; and so on for Tables 47 to 66.

Table A discloses 47 sets of meanings of the variables $R^2$, $R^3$, $R^4$, $R^5$ and $R^6$ in a compound of formula Ib.

TABLE A

| | $R^2$ | $R^3$ | $R^4$ | $R^5$ | $R^6$ |
|---|---|---|---|---|---|
| A.1.001 | n-propyl | ethyl | ethyl | H | methyl |
| A.1.002 | n-propyl | methyl | cyclopropyl | H | methyl |
| A.1.003 | n-propyl | methyl | isopropyl | H | methyl |
| A.1.004 | n-propyl | —$CH_2$—$CH_2$—$CH_2$—$CH_2$— | | H | methyl |
| A.1.005 | n-propyl | methyl | methyl | H | methyl |

TABLE A-continued

|  | R² | R³ | R⁴ | R⁵ | R⁶ |
|---|---|---|---|---|---|
| A.1.006 | n-propyl | ethyl | H | H | methyl |
| A.1.007 | n-propyl | methyl | H | H | methyl |
| A.1.008 | n-propyl | isopropyl | H | H | methyl |
| A.1.09 | prop-2-enyl | ethyl | ethyl | H | methyl |
| A.1.010 | prop-2-enyl | methyl | cyclopropyl | H | methyl |
| A.1.011 | prop-2-enyl | methyl | isopropyl | H | methyl |
| A.1.012 | prop-2-enyl | —CH₂—CH₂—CH₂—CH₂— | | H | methyl |
| A.1.013 | prop-2-enyl | methyl | methyl | H | methyl |
| A.1.014 | prop-2-enyl | ethyl | H | H | methyl |
| A.1.015 | prop-2-enyl | isopropyl | H | H | methyl |
| A.1.016 | prop-2-enyl | ethyl | methyl | H | methyl |
| A.1.017 | isopropyl | ethyl | methyl | H | methyl |
| A.1.018 | isopropyl | ethyl | methyl | methyl | methyl |
| A.1.019 | propargyl | ethyl | methyl | H | methyl |
| A.1.020 | n-propyl | ethyl | methyl | H | methyl |
| A.1.021 | prop-2-enyl | ethyl | methyl | methyl | methyl |
| A.1.022 | n-propyl | ethyl | methyl | methyl | methyl |
| A.1.023 | propargyl | ethyl | methyl | methyl | methyl |
| A.1.024 | 3,3-difluoropropyl | ethyl | methyl | H | methyl |
| A.1.025 | 3,3,3-trifluoropropyl | ethyl | methyl | methyl | methyl |
| A.1.026 | 3,3,3-trifluoropropyl | ethyl | methyl | H | methyl |
| A.1.027 | 3,3-difluoroprop-2-enyl | ethyl | methyl | H | methyl |
| A.1.028 | n-propyl | ethyl | methyl | H | ethyl |
| A.1.029 | prop-2-enyl | ethyl | methyl | H | ethyl |
| A.1.030 | propargyl | ethyl | methyl | H | ethyl |
| A.1.031 | n-propyl | ethyl | methyl | H | methoxymethyl |
| A.1.032 | prop-2-enyl | ethyl | methyl | H | methoxymethyl |
| A.1.033 | propargyl | ethyl | methyl | H | methoxymethyl |
| A.1.034 | 2,2-dimethyl-propyl | ethyl | methyl | H | methyl |
| A.1.035 | 2-methyl-butyl | ethyl | methyl | H | methyl |
| A.1.036 | 2,2-dimethyl-butyl | ethyl | methyl | H | methyl |
| A.1.037 | cyclopropyl | ethyl | methyl | H | methyl |
| A.1.038 | cyclobutyl | ethyl | methyl | H | methyl |
| A.1.039 | cyclopentyl | ethyl | methyl | H | methyl |
| A.1.040 | cyclopent-3-enyl | ethyl | methyl | H | methyl |
| A.1.041 | 3-methyl-but-2-enyl | ethyl | methyl | H | methyl |
| A.1.042 | but-2-enyl | ethyl | methyl | H | methyl |
| A.1.043 | cyclopropyl-methyl | ethyl | methyl | H | methyl |
| A.1.044 | cyclobutyl-methyl | ethyl | methyl | H | methyl |
| A.1.045 | cyclopentyl-methyl | ethyl | methyl | H | methyl |
| A.1.046 | cyclopent-3-enyl-methyl | ethyl | methyl | H | methyl |
| A.1.047 | n-propyl | —CH₂—CH₂—CH₂— | | H | methyl |

Tables 1, 23 and 45: Tables 1, 23 and 45 disclose 47 compounds of formula (I), 47 compounds of formula (Ia) and 47 compounds of formula (Ib) respectively wherein $R^1$ is hydrogen and each of the variables $R^2$, $R^3$, $R^4$, $R^5$ and $R^6$ has the specific meaning given in the corresponding row of Table A. For example;

compound 1.1.016 has the following structure:

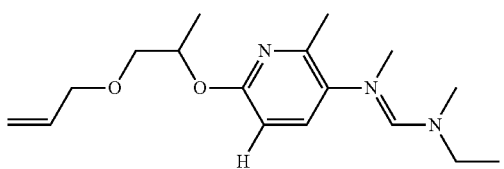

compound 23.1.043 has the following structure:

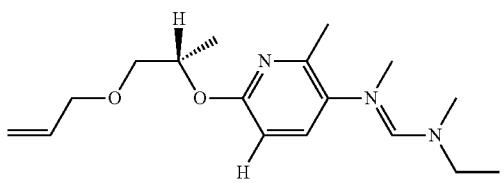

compound 45.1.043 has the following structure:

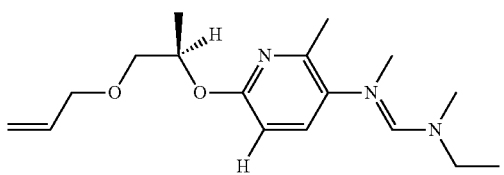

Tables 2, 24 and 46: Tables 2, 24 and 46 disclose 47 compounds of formula (I), 47 compounds of formula (Ia) and 47 compounds of formula (Ib) respectively wherein $R^1$ is chloro and each of the variables $R^2$, $R^3$, $R^4$, $R^5$ and $R^6$ has the specific meaning given in the corresponding row of Table A.

Tables 3, 25 and 47: Tables 3, 25 and 47 disclose 47 compounds of formula (I), 47 compounds of formula (Ia) and 47 compounds of formula (Ib) respectively wherein $R^1$ is bromo and each of the variables $R^2$, $R^3$, $R^4$, $R^5$ and $R^6$ has the specific meaning given in the corresponding row of Table A.

Tables 4, 26 and 48: Tables 4, 26 and 48 disclose 47 compounds of formula (I), 47 compounds of formula (Ia) and 47 compounds of formula (Ib) respectively wherein $R^1$ is iodo and each of the variables $R^2$, $R^3$, $R^4$, $R^5$ and $R^6$ has the specific meaning given in the corresponding row of Table A.

Tables 5, 27 and 49: Tables 5, 27 and 49 disclose 47 compounds of formula (I), 47 compounds of formula (Ia) and 47 compounds of formula (Ib) respectively wherein $R^1$ is methyl and each of the variables $R^2$, $R^3$, $R^4$, $R^5$ and $R^6$ has the specific meaning given in the corresponding row of Table A.

Tables 6, 28 and 50: Tables 6, 28 and 50 disclose 47 compounds of formula (I), 47 compounds of formula (Ia) and 47 compounds of formula (Ib) respectively wherein $R^1$ is ethyl and each of the variables $R^2$, $R^3$, $R^4$, $R^5$ and $R^6$ has the specific meaning given in the corresponding row of Table A.

Tables 7, 29 and 51: Tables 7, 29 and 51 disclose 47 compounds of formula (I), 47 compounds of formula (Ia) and 47 compounds of formula (Ib) respectively wherein $R^1$ is cyclopropyl and each of the variables $R^2$, $R^3$, $R^4$, $R^5$ and $R^6$ has the specific meaning given in the corresponding row of Table A.

Tables 8, 30 and 52: Tables 8, 30 and 52 disclose 47 compounds of formula (I), 47 compounds of formula (Ia) and 47 compounds of formula (Ib) respectively wherein $R^1$ is trifluoromethyl and each of the variables $R^2$, $R^3$, $R^4$, $R^5$ and $R^6$ has the specific meaning given in the corresponding row of Table A.

Tables 9, 31 and 53: Tables 9, 31 and 53 disclose 47 compounds of formula (I), 47 compounds of formula (Ia) and 47 compounds of formula (Ib) respectively wherein $R^1$ is difluoromethyl and each of the variables $R^2$, $R^3$, $R^4$, $R^5$ and $R^6$ has the specific meaning given in the corresponding row of Table A.

Tables 10, 32 and 54: Tables 10, 32 and 54 disclose 47 compounds of formula (I), 47 compounds of formula (Ia) and 47 compounds of formula (Ib) respectively wherein $R^1$ is ethynyl and each of the variables $R^2$, $R^3$, $R^4$, $R^5$ and $R^6$ has the specific meaning given in the corresponding row of Table A.

Tables 11, 33 and 55: Tables 11, 33 and 55 disclose 47 compounds of formula (I), 47 compounds of formula (Ia) and 47 compounds of formula (Ib) respectively wherein $R^1$ is methoxy and each of the variables $R^2$, $R^3$, $R^4$, $R^5$ and $R^6$ has the specific meaning given in the corresponding row of Table A.

Tables 12, 34 and 56: Tables 12, 34 and 56 disclose 47 compounds of formula (I), 47 compounds of formula (Ia) and 47 compounds of formula (Ib) respectively wherein $R^1$ is difluoromethoxy and each of the variables $R^2$, $R^3$, $R^4$, $R^5$ and $R^6$ has the specific meaning given in the corresponding row of Table A.

Tables 13, 35 and 57: Tables 13, 35 and 57 disclose 47 compounds of formula (I), 47 compounds of formula (Ia) and 47 compounds of formula (Ib) respectively wherein $R^1$ is methylamino and each of the variables $R^2$, $R^3$, $R^4$, $R^5$ and $R^6$ has the specific meaning given in the corresponding row of Table A.

Tables 14, 36 and 58: Tables 14, 36 and 58 disclose 47 compounds of formula (I), 47 compounds of formula (Ia) and 47 compounds of formula (Ib) respectively wherein $R^1$ is dimethylamino and each of the variables $R^2$, $R^3$, $R^4$, $R^5$ and $R^6$ has the specific meaning given in the corresponding row of Table A.

Tables 15, 37 and 59: Tables 15, 37 and 59 disclose 47 compounds of formula (I), 47 compounds of formula (Ia) and 47 compounds of formula (Ib) respectively wherein $R^1$ is N-methylsulfonamide, wherein the broken line below indicates the point of attachment of the group $R^1$ to the remainder of the compound and each of the variables $R^2$, $R^3$, $R^4$, $R^5$ and $R^6$ has the specific meaning given in the corresponding row of Table A.

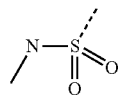

Tables 16, 38 and 60: Tables 16, 38 and 60 disclose 47 compounds of formula (I), 47 compounds of formula (Ia) and 47 compounds of formula (Ib) respectively wherein $R^1$ is N,N-dimethylsulfonamide, wherein the broken line below indicates the point of attachment of the group $R^1$ to the remainder of the compound and each of the variables $R^2$, $R^3$, $R^4$, $R^5$ and $R^6$ has the specific meaning given in the corresponding row of Table A.

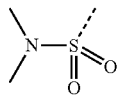

Tables 17, 39 and 61: Tables 17, 39 and 61 disclose 47 compounds of formula (I), 47 compounds of formula (Ia) and 47 compounds of formula (Ib) respectively wherein $R^1$ is fluoro and each of the variables $R^2$, $R^3$, $R^4$, $R^5$ and $R^6$ has the specific meaning given in the corresponding row of Table A.

Tables 18, 40 and 62: Tables 18, 40 and 62 disclose 47 compounds of formula (I), 47 compounds of formula (Ia) and 47 compounds of formula (Ib) respectively wherein $R^1$ is acetyl and each of the variables $R^2$, $R^3$, $R^4$, $R^5$ and $R^6$ has the specific meaning given in the corresponding row of Table A.

Tables 19, 41 and 63: Tables 19, 41 and 63 disclose 47 compounds of formula (I), 47 compounds of formula (Ia) and 47 compounds of formula (Ib) respectively wherein $R^1$ is methoxyformyl wherein the broken line below indicates the point of attachment of the group $R^1$ to the remainder of the compound and each of the variables $R^2$, $R^3$, $R^4$, $R^5$ and $R^6$ has the specific meaning given in the corresponding row of Table A.

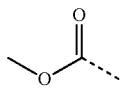

Tables 20, 42 and 64: Tables 20, 42 and 64 disclose 47 compounds of formula (I), 47 compounds of formula (Ia) and 47 compounds of formula (Ib) respectively wherein $R^1$ is hydroxy and each of the variables $R^2$, $R^3$, $R^4$, $R^5$ and $R^6$ has the specific meaning given in the corresponding row of Table A.

Tables 21, 43 and 65: Tables 21, 43 and 65 disclose 47 compounds of formula (I), 47 compounds of formula (Ia) and 47 compounds of formula (Ib) respectively wherein $R^1$ is fluoromethyl and each of the variables $R^2$, $R^3$, $R^4$, $R^5$ and $R^6$ has the specific meaning given in the corresponding row of Table A.

Tables 22, 44 and 66: Tables 22, 44 and 66 disclose 47 compounds of formula (I), 47 compounds of formula (Ia) and 47 compounds of formula (Ib) respectively wherein $R^1$ is cyano and each of the variables $R^2$, $R^3$, $R^4$, $R^5$ and $R^6$ has the specific meaning given in the corresponding row of Table A.

It has now been found that the compounds of formula (I) according to the invention have, for practical purposes, a very advantageous spectrum of activities for protecting useful plants against diseases that are caused by phytopathogenic microorganisms, such as fungi, bacteria or viruses, in particular against diseases that are caused by fungi.

The invention therefore also relates to a method of controlling or preventing infestation of useful plants by phytopathogenic microorganisms, wherein a compound of formula (I) is applied as active ingredient to the plants, to parts thereof or the locus thereof.

The term "plants" refers to all physical parts of a plant, including seeds, seedlings, saplings, roots, tubers, stems, stalks, foliage, and fruits.

The term "locus" as used herein means fields in or on which plants are growing, or where seeds of cultivated plants are sown, or where seed will be placed into the soil. It includes soil, seeds, and seedlings, as well as established vegetation.

The compounds of formula I can be used in the agricultural sector and related fields of use e.g. as active ingredients for controlling plant pests or on non-living materials for control of spoilage microorganisms or organisms potentially harmful to man.

The compounds of formula (I) according to the invention are distinguished by excellent activity at low rates of application, by being well tolerated by plants and by being environmentally safe. They have very useful curative, preventive and systemic properties and are used for protecting numerous useful plants. The compounds of formula (I) can be used to inhibit or destroy the diseases that occur on plants or parts of plants of different crops of useful plants, while at the same time protecting also those parts of the plants that grow later from phytopathogenic micro-organisms.

It is possible to use compounds of formula I as fungicide. The term "fungicide" as used herein means a compound that controls, modifies, or prevents the growth of fungi. The term "fungicidally effective amount" means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

A preferred method of applying a compound of formula (I) is foliar application. The frequency of application and the rate of application will depend on the risk of infestation by the corresponding pathogen. However, the compounds of formula (I) may also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field.

It is also possible to use compounds of formula (I) as dressing agents for the treatment of plant propagation material, in particular of seeds and plant cuttings (e.g. rice), for the protection against fungal infections as well as against phytopathogenic fungi occurring in the soil.

The propagation material can be treated with a composition comprising a compound of formula I before planting: seed, for example, can be dressed before being sown. The active ingredients according to the invention can also be applied to grains (coating), either by impregnating the seeds in a liquid formulation or by coating them with a solid formulation. The composition can also be applied to the planting site when the propagation material is being planted, for example, to the seed furrow during sowing. The invention relates also to such methods of treating plant propagation material and to the plant propagation material so treated.

The term "plant propagation material" denotes all generative parts of a plant, for example seeds or vegetative parts of plants such as cuttings and tubers. It includes seeds in the strict sense, as well as roots, fruits, tubers, bulbs, rhizomes, and parts of plants.

Furthermore the compounds of formula (I) according to the invention may be used for controlling fungi in related areas, for example in the protection of technical materials, including wood and wood related technical products, in food storage or in hygiene management.

In addition, the invention could be used to protect non-living materials from fungal attack, e.g. lumber, wall boards and paint.

The compounds of formula I are for example, effective against Fungi and fungal vectors of disease as well as phytopathogenic bacteria and viruses. These Fungi and fungal vectors of disease as well as phytopathogenic bacteria and viruses are for example:

*Absidia corymbifera, Alternaria* spp, *Aphanomyces* spp, *Ascochyta* spp, *Aspergillus* spp. including *A. flavus, A. fumigatus, A. nidulans, A. niger, A. terrus, Aureobasidium* spp. including *A. pullulans, Blastomyces dermatitidis, Blumeria graminis, Bremia lactucae, Botryosphaeria* spp. including *B. dothidea, B. obtusa, Botrytis* spp. including *B. cinerea, Candida* spp. including *C. albicans, C. glabrata, C. krusei, C. lusitaniae, C. parapsilosis, C. tropicalis, Cephaloascus fragrans, Ceratocystis* spp, *Cercospora* spp. including *C. arachidicola, Cercosporidium personatum, Cladosporium* spp, *Claviceps purpurea, Coccidioides immitis, Cochliobolus* spp, *Colletotrichum* spp. including *C. musae, Cryptococcus neoformans, Diaporthe* spp, *Didymella* spp, *Drechslera* spp, *Elsinoe* spp, *Epidermophyton* spp, *Erwinia amylovora, Erysiphe* spp. including *E. cichoracearum, Eutypa lata, Fusarium* spp. including *F. culmorum, F. graminearum, F. langsethiae, F. moniliforme, F. oxysporum, F. proliferatum, F. subglutinans, F. solani, Gaeumannomyces graminis, Gibberella fujikuroi, Gloeodes pomigena, Gloeosporium musarum, Glomerella cingulate, Guignardia bidwellii, Gymnosporangium juniperi-virginianae, Helminthosporium* spp, *Hemileia* spp, *Histoplasma* spp. including *H. capsulatum, Laetisaria fuciformis, Leptographium lindbergi, Leveillula taurica, Lophodermium seditiosum, Microdochium nivale, Microsporum* spp, *Monilinia* spp, *Mucor* spp, *Mycosphaerella* spp. including *M. graminicola, M. pomi, Oncobasidium theobromaeon, Ophiostoma piceae, Paracoccidioides* spp, *Penicillium* spp. including *P. digitatum, P. italicum, Petriellidium* spp, *Peronosclerospora* spp. Including *P. maydis, P. philippinensis* and *P. sorghi, Peronospora* spp, *Phaeosphaeria nodorum, Phakopsora pachyrhizi, Phellinus igniarus, Phialophora* spp, *Phoma* spp, *Phomopsis viticola, Phytophthora* spp. including *P. infestans, Plasmopara* spp. including *P. halstedii, P. viticola, Pleospora* spp., *Podosphaera* spp. including *P. leucotricha, Polymyxa graminis, Polymyxa betae, Pseudocercosporella herpotrichoides, Pseudomonas* spp, *Pseudoperonospora* spp. including *P. cubensis, P. humuli, Pseudopeziza tracheiphila, Puccinia* Spp. including *P. hordei, P. recondita, P. striiformis, P. triticina, Pyrenopeziza* spp, *Pyrenophora* spp, *Pyricularia* spp. including *P. oryzae, Pythium* spp. including *P. ultimum, Ramularia* spp, *Rhizoctonia* spp, *Rhizomucor pusillus, Rhizopus arrhizus, Rhynchosporium* spp, *Scedosporium* spp. including *S. apiospermum* and *S. prolificans, Schizothyrium pomi, Sclerotinia* spp, *Sclerotium* spp, *Septoria* spp, including *S. nodorum, S. tritici, Sphaerotheca macularis, Sphaerotheca fusca (Sphaerotheca fuliginea), Sporothorix* spp, *Stagonospora nodorum, Stemphylium* spp, *Stereum hirsutum, Thanatephorus cucumeris, Thielaviopsis basicola, Tilletia* spp, *Trichoderma* spp. including *T. harzianum, T. pseudokoningii, T. viride, Trichophyton* spp, *Typhula* spp, *Uncinula necator, Urocystis* spp, *Ustilago* spp, *Venturia* spp. including *V. inaequalis, Verticillium* spp, and *Xanthomonas* spp.

Crops of useful plants in which the composition according to the invention can be used include perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

Crops are to be understood as being those which are naturally occurring, obtained by conventional methods of breeding, or obtained by genetic engineering. They include crops which contain so-called output traits (e.g. improved storage stability, higher nutritional value and improved flavour).

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®.

Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

The compounds of formula (I) can be used in unmodified form or, preferably, together with carriers and adjuvants conventionally employed in the art of formulation.

Therefore the invention also relates to compositions for controlling and protecting against phytopathogenic microorganisms, comprising a compound of formula (I) and an inert carrier, and to a method of controlling or preventing infestation of useful plants by phytopathogenic microorganisms, wherein a composition, comprising a compound of formula (I) as active ingredient and an inert carrier, is applied to the plants, to parts thereof or the locus thereof.

To this end compounds of formula (I) and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants (auxiliaries) can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

A formulation, i.e. a composition comprising the compound of formula (I) and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula (I), 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

Normally, in the management of a crop a grower would use one or more other agronomic chemicals in addition to the compound of the present invention. Examples of agronomic chemicals include pesticides, such as acaricides, bactericides, fungicides, herbicides, insecticides, nematicides, as well as plant nutrients and plant fertilizers.

Accordingly, the present invention provides a composition comprising a compound of formula (I) according to the present invention together with one or more pesticides, plant nutrients or plant fertilizers. The combination may also encompass specific plant traits incorporated into the plant using any means, for example conventional breeding or genetic modification. Such compositions may also contain one or more inert carriers as described above.

The invention also provides for the use of provides a composition comprising a compound of formula (I) according to the present invention together with one or more pesticides, plant nutrients or plant fertilizers. The combination may also encompass specific plant traits incorporated into the plant using any means, for example conventional breeding or genetic modification.

Suitable examples of plant nutrients or plant fertilizers are calcium sulfate ($CaSO_4$), calcium nitrate ($Ca(NO_3)_2.4H_2O$), calcium carbonate ($CaCO_3$), potassium nitrate ($KNO_3$), magnesium sulfate ($MgSO_4$), potassium hydrogen phosphate ($KH_2PO_4$), manganese sulfate ($MnSO_4$), copper sulfate ($CuSO_4$), zinc sulfate ($ZnSO_4$), nickel chloride ($NiCl_2$), cobalt sulfate ($CoSO_4$), potassium hydroxide ($KOH$), sodium chloride ($NaCl$), boric acid ($H_3BO_3$) and metal salts thereof ($Na_2MoO_4$). The nutrients may be present in an amount of 5% to 50% by weight, preferably of 10% to 25% by weight or of 15% to 20% by weight each. Preferred additional nutrients are urea ($(NH_2)_2CO$), melamine ($C_3H_6N_6$), potassium oxide ($K_2O$), and inorganic nitrates. The most preferred additional plant nutrient is potassium oxide. Where the preferred additional nutrient is urea, it is present in an amount of generally 1% to 20% by weight, preferably 2% to 10% by weight or of 3% to 7% by weight.

Suitable examples of pesticides are acycloamino acid fungicides, aliphatic nitrogen fungicides, amide fungicides, anilide fungicides, antibiotic fungicides, aromatic fungicides, arsenical fungicides, aryl phenyl ketone fungicides, benzamide fungicides, benzanilide fungicides, benzimidazole fungicides, benzothiazole fungicides, botanical fungicides, bridged diphenyl fungicides, carbamate fungicides, carbanilate fungicides, conazole fungicides, copper fungicides, dicarboximide fungicides, dinitrophenol fungicides, dithiocarbamate fungicides, dithiolane fungicides, furamide fungicides, furanilide fungicides, hydrazide fungicides, imidazole fungicides, mercury fungicides, morpholine fungicides, organophosphorous fungicides, organotin fungicides, oxathiin fungicides, oxazole fungicides, phenylsulfamide fungicides, polysulfide fungicides, pyrazole fungicides, pyridine fungicides, pyrimidine fungicides, pyrrole fungicides, quaternary ammonium fungicides, quinoline fungicides, quinone fungicides, quinoxaline fungicides, strobilurin fungicides, sulfonanilide fungicides, thiadiazole fungicides, thiazole fungicides, thiazolidine fungicides, thiocarbamate fungicides, thiophene fungicides, triazine fungicides, triazole fungicides, triazolopyrimidine fungicides, urea fungicides, valinamide fungicides, zinc fungicides, Benzoylureas, carbamates, chloronicotinyls, diacylhydrazines, diamides, fiproles, macrolides, nitroimines, nitromethylenes, organochlorines, organophosphates, organosilicons, organotins, phenylpyrazoles, phosphoric esters, pyrethroids, spinosyns, tetramic acid derivatives, tetronic acid derivatives, Antibiotic nematicides, avermectin nematicides, botanical nematicides, carbamate nematicides, oxime carbamate nematicides, organophosphorus nematicides, nematophagous fungi or bacteria, amide herbicides, anilide herbicides, arsenical herbicides, arylalanine herbicides, aryloxyphenoxypropionic herbicides, benzofuranyl herbicides, benzoic acid herbicides, benzothiazole herbicides, benzoylcyclohexanedione herbicides, carbamate herbicides, carbanilate herbicides, chloroacetanilide herbicides, chlorotriazine herbicides, cyclohexene oxmie herbicides, cyclopropylisoxazole herbicides, dicarboximide herbicides, dinitroaniline herbicides, dinitrophenol herbicides, diphenyl ether herbicides, dithiocarbamate herbicides, fluoroalkyltriazine herbicides, halogenated aliphatic herbicides, imidazolinone herbicides, inorganic herbicides, methoxytriazine herbicides, methylthiotriazine herbicides, nitrile herbicides, nitrophenyl ether herbicides, organophosphorous herbicides, oxadiazolone herbicides, oxazole herbicides, phenoxy herbicides, phenoxyacetic herbicides, phenoxybutyric herbicides, phenoxypropionic herbicides, phenylenediamine herbicides, phenylurea herbicides, phthalic acid herbicides, picolinic acid herbicides, pyrazole herbicides, pyridazine herbicides, pyridazinone herbicides, pyridine herbicides, pyrimidinediamine herbicides, pyrimidinyloxybenzylamine herbicides, pyrimidinylsulfonylurea herbicides, quaternary ammonium herbicides, quinolinecarboxylic acid herbicides, sulfonamide herbicides, sulfonanilide herbicides, sulfonylurea herbicides, thiadiazolylurea herbicides, thioamide herbicides, thiocarbamate herbicides, thiocarbonate herbicides, thiourea herbicides, triazine herbicides, triazinone herbicides, triazinylsulfonylurea herbicides, triazole herbicides, triazolone herbicides, triazolopyrimidine herbicides, uracil herbicides, urea herbicides, microbials, plant extracts, pheromones, macrobials and other biologicals.

The following non-limiting Examples illustrate the above-described invention in greater detail without limiting it. Those skilled in the art will promptly recognise appropriate variations from the procedures both as to reactants and as to reaction conditions and techniques. All references mentioned herein are incorporated by reference in their entirety.

SYNTHETIC EXAMPLES

Using techniques analogous to those described in WO 12/146125 (pp. 370-378) and further techniques known to the person skilled in the art, for example as found in WO 08/101682 (pp. 22-33), compounds of formula (I) may be prepared.

Preparation of (2R)-1-propoxypropan-2-ol

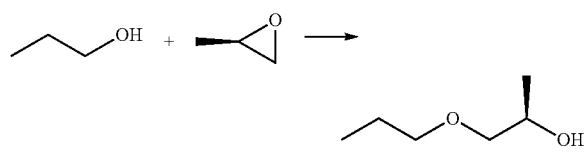

To an ice-bath cooled solution of THF (400 mL) under inert atmosphere (Ar) and sodium hydride (12 g, 490 mmol, 5 equiv.) 1-propanol (40 mL, 490 mmol, 5 equiv) was added dropwise. The ice bath was removed and the reaction mixture was stirred at room temperature for 30 minutes then (2R)-2-methyloxirane (5.8 g, 99 mmol) was added dropwise and the reaction was stirred for 18 h under heating at 50° C. After this time, GC-MS and NMR indicated that the starting material was consumed and the reaction mixture was allowed to reach room temperature before quenching with aqueous NH$_4$Cl solution and extracting with dichloromethane. The organic layer was dried over anhydrous Na$_2$SO$_4$ and filtered. The solvent was removed in vacuo (not dropping below 200 mbar) at 30° C. and provided the title compound (4.4 g, 38% yield) as a yellow liquid.

$^1$H NMR (400 MHz, CDCl$_3$): δ (ppm) 4.00-3.87 (1 H, m) 3.50-3.40 (m, 3H), 3.30-3.20 (m, 1H), 2.64 (d, 1H), 1.61 (m, 2H), 1.12 (d, 3H), 0.95 (t, 3H)

Preparation of N'-[5-bromo-2-methyl-6-[(1S)-1-methyl-2-propoxy-ethoxy]-3-pyridyl]-N-ethyl-N-methyl-formamidine

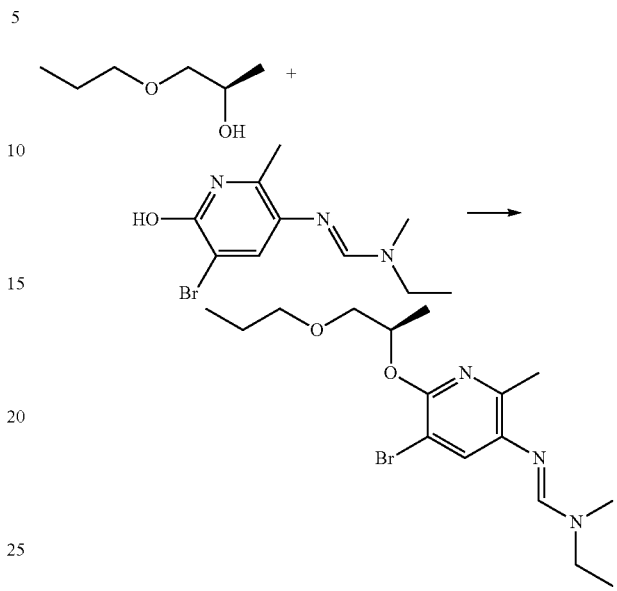

To a stirring suspension of N'-(5-bromo-6-hydroxy-2-methyl-3-pyridyl)-N-ethyl-N-methyl-formamidine (0.75 g, 2.8 mmol) in THF (15 mL), (2R)-1-propoxypropan-2-ol (0.36 g, 3 mmol, 1.1 equiv) and triphenylphosphine (0.80 g, 3 mmol, 1.1 equiv) were added at room temperature under inert atmosphere (Ar). To this mixture, DIAD (diisopropyl diazodicarboxylate) (0.60 mL, 3 mmol, 1.1 equiv) was added dropwise over 10 minutes while keeping the temperature below 40° C. The reaction mixture was stirred for 24 h at room temperature. After this time, LC-MS indicated that the starting material had been nearly consumed and the reaction mixture was quenched with water (40 mL). The water phase was extracted with ethyl acetate (3×50 mL). The organic layer was dried over anhydrous Na$_2$SO$_4$ and filtered. The solvent was removed in vacuo to give a brown residue, which was purified by preparative reverse phase chromatography to afford the desired (0.10 g, 10% yield).

$^1$H NMR (400 MHz, CDCl$_3$): δ (ppm) 7.45-7.30 (broad s, 1 H), 7.24 (s, 1 H), 5.40-5.30 (m, 1 H), 3.70-3.60 (m, 1 H), 3.55-3.45 (m, 3H), 3.45-3.30 (broad m, 2H), 3.00 (s, 3H), 2.35 (s, 3H), 1.65-1.50 (m, 2H), 1.35 (m, 3H), 1.20 (m, 3H), 0.90 (t, 3H).

Preparation of N'-[5-bromo-2-methyl-6-[(1R)-1-methyl-2-propoxy-ethoxy]-3-pyridyl]-N-ethyl-N-methyl-formamidine

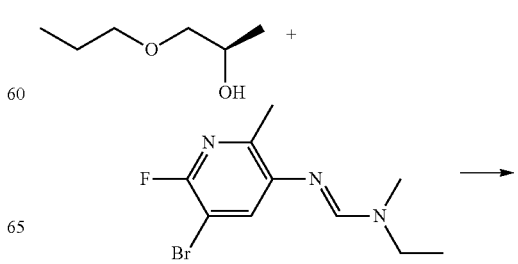

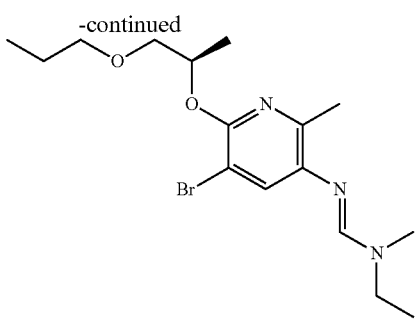

To an ice-bath cooled solution of (2R)-1-propoxypropan-2-ol (0.103 g, 0.88 mmol, 1.2 equiv) in DMF (4 mL) under inert atmosphere (Ar), potassium tertbutoxide (0.25 g, 2.19 mmol, 3 equiv) and triphenylphosphine (0.14 g, 0.55 mmol, 1.5 equiv) was added. The reaction mixture was stirred for 20 minutes before N'-(5-bromo-6-fluoro-2-methyl-3-pyridyl)-N-ethyl-N-methyl-formamidine (0.20 g, 0.73 mmol) was added. The reaction mixture was stirred for 4 h at room temperature and was quenched with water upon completion. The water phase was extracted with ethyl acetate (2×50 mL). The organic layers were combined, washed with water (3×50 mL), dried over anhydrous Na$_2$SO$_4$, and filtered. The solvent was removed in vacuo to give a brown residue, which was purified by preparative reverse phase chromatography to afford the desired compound (0.130 g, 13% yield).

$^1$H NMR (400 MHz, CDCl$_3$): δ (ppm) 7.45-7.30 (broad s, 1 H), 7.24 (s, 1 H), 5.40-5.30 (m, 1 H), 3.70-3.60 (m, 1 H), 3.55-3.45 (m, 3H), 3.50-3.30 (broad m, 2H), 3.00 (s, 3H), 2.35 (s, 3H), 1.65-1.50 (m, 2H), 1.35 (m, 3H), 1.20 (m, 3H), 0.90 (t, 3H).

Preparation of N'-[5-bromo-2-methyl-6-(1-methyl-2-propoxy-ethoxy)-3-pyridyl]-N-ethyl-N-methyl-formamidine

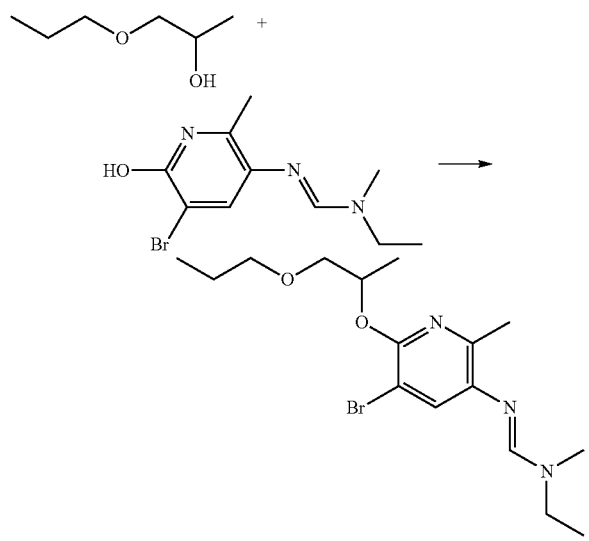

To a stirring suspension of N'-(5-bromo-6-hydroxy-2-methyl-3-pyridyl)-N-ethyl-N-methyl-formamidine (6.0 g, 22.05 mmol) in THF (30 mL), 1-propoxypropan-2-ol (3.53 mL, 26.46 mmol, 1.2 equiv) and triphenylphosphine (6.94 g, 26.46 mmol, 1.2 equiv) were added at room temperature under inert atmosphere (Ar). To this mixture, DIAD (diisopropyl diazodicarboxylate) (5.21 mL, 26.46 mmol, 1.2 equiv) was added dropwise over 10 minutes while keeping the temperature below 40° C. The reaction mixture was stirred for 1.5 h at room temperature. After this time, LC-MS indicated that the starting material had been consumed and the reaction mixture was concentrated in vacuo. Heptane was added to the residue and the mixture was cooled with an ice bath to recrystallize triphenylphosphine oxide. The brown residue was purified by combiflash column chromatography (silica gel, heptane/ethyl acetate, v/v=90/10 to 4/1). Fractions containing the pure compound were collected and concentrated in vacuo to give the title compound (7.80 g, 95% yield) as a light yellow oil.

$^1$H NMR (400 MHz, CDCl$_3$): δ (ppm) 7.45-7.30 (broad s, 1 H), 7.24 (s, 1 H), 5.40-5.30 (m, 1 H), 3.70-3.60 (m, 1 H), 3.55-3.45 (m, 3H), 3.45-3.30 (broad m, 2H), 3.00 (s, 3H), 2.35 (s, 3H), 1.65-1.50 (m, 2H), 1.35 (m, 3H), 1.20 (m, 3H), 0.90 (t, 3H).

Preparation of N'-[5-cyano-2-methyl-6-(1-methyl-2-propoxy-ethoxy)-3-pyridyl]-N-ethyl-N-methyl-formamidine

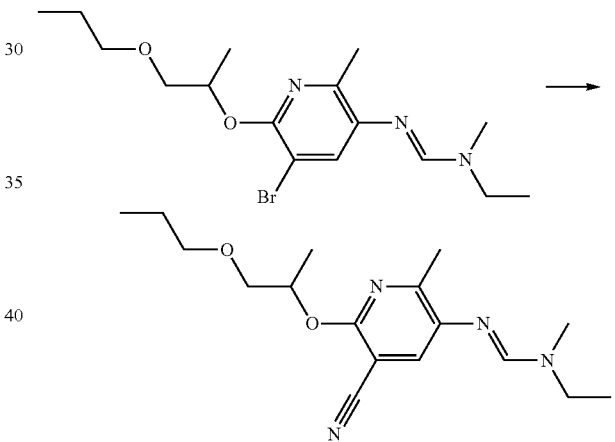

To a stirred solution of N'-[5-bromo-2-methyl-6-(1-methyl-2-propoxy-ethoxy)-3-pyridyl]-N-ethyl-N-methyl-formamidine (0.25 g, 0.67 mmol) in DMF (1 mL) under inert atmosphere (Ar), zinc cyanide (0.087 g, 0.74 mmol, 1.1 equiv) and tetrakis(triphenylphosphine)palladium (0.23 g, 0.20 mmol, 0.3 equiv) were added and the reaction mixture was stirred for 18 h under heating at 120° C. After this time, TLC and LC-MS indicated that the starting material was consumed and the reaction mixture was allowed to reach room temperature before quenching with water. The water phase was extracted with ethyl acetate (2×30 mL). The organic layer was washed with brine (3×50 mL), dried over anhydrous Na$_2$SO$_4$ and filtered. The solvent was removed in vacuo to give a brown residue, which was purified by combiflash column chromatography (silica gel, heptane/ethyl acetate, v/v=90/10 to 70/30). Fractions containing the pure compound were collected and concentrated in vacuo to give the title compound (0.207 g, 97% yield) as a colorless oil.

$^1$H NMR (400 MHz, CDCl$_3$): δ (ppm) 7.45-7.30 (broad s, 1 H), 7.20 (s, 1 H), 5.50-5.40 (m, 1 H), 3.70-3.60 (m, 1 H), 3.55-3.40 (m, 3H), 3.45-3.30 (broad m, 2H), 3.00 (s, 3H), 2.40 (s, 3H), 1.65-1.50 (m, 2H), 1.35 (m, 3H), 1.20 (m, 3H), 0.90 (t, 3H).

Preparation of 3-chloro-6-methyl-5-nitro-pyridin-2-ol

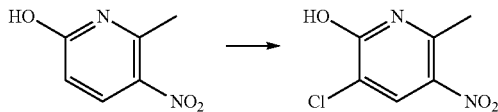

To an ice-bath cooled suspension of 6-methyl-5-nitro-pyridin-2-ol (0.50 g, 3.24 mmol) in acetonitrile (5 mL) under inert atmosphere (Ar), was added N-chlorosuccinimide (0.43 g, 3.24 mmol, 1 equiv) portionwise. The reaction mixture was stirred for 20 h under heating at 67° C. At this time, LC-MS indicated that the starting material was consumed and the reaction mixture was cooled to 0° C. and the precipitate was filtered to give the title compound (0.36 g, 48% yield) as a beige-white solid.

$^1$H NMR (400 MHz, CD$_3$OD): δ (ppm) 8.5 (s, 1H), 2.7 (s, 3H).

Preparation of 5-chloro-2-methyl-3-nitro-6-(o-tolyl-methoxy)pyridine

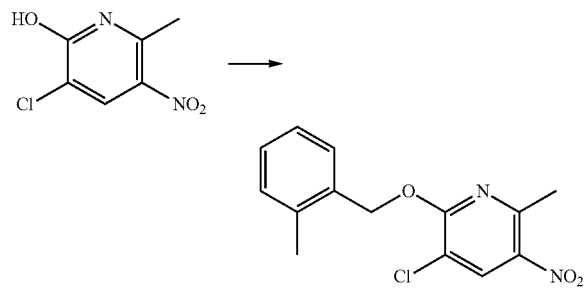

To a stirred solution of o-tolylmethanol (3.99 g, 32.1 mmol, 1.2 equiv) in THF (100 mL), 3-chloro-6-methyl-5-nitro-pyridin-2-ol (5.30 g, 26.7 mmol) and triphenylphosphine (8.41 g, 32.1 mmol, 1.2 equiv) were added at room temperature under inert atmosphere (Ar). To this mixture, DIAD (diisopropyl diazodicarboxylate) (6.58 mL, 33.4 mmol, 1.25 equiv) was added dropwise over 10 minutes while keeping the temperature below 40° C. The reaction mixture was stirred for 16 h at room temperature. At this time, LC-MS indicated that the starting material was consumed and the reaction mixture was quenched with water (20 mL). A precipitate formed and was filtered and washed with a mixture of methanol/water (v/v=5/1), suspended in toluene and concentrated in vacuo to give the title compound (5.28 g, 47% yield) as a yellow solid.

$^1$H NMR (400 MHz, DMSO): δ (ppm)=8.60 (s, 1 H), 7.45 (d, 1H), 7.30-7.20 (m, 3H), 5.50 (s, 2H), 2.70 (s, 3H), 2.35 (s, 3H).

Preparation of 6-benzyloxy-5-chloro-2-methyl-pyridin-3-amine

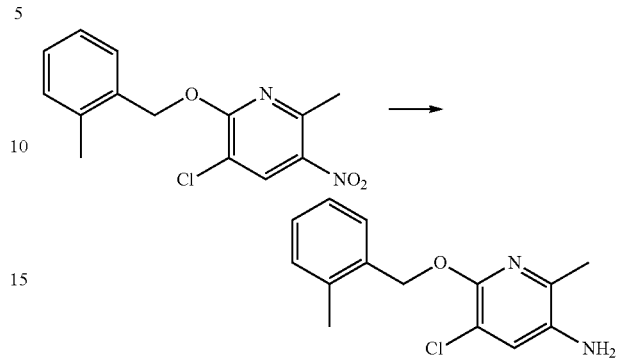

A solution of 2-benzyloxy-3-chloro-6-methyl-5-nitro-pyridine (250 mg, 0.90 mmol), 10% platinum on carbon (12 mg, 0.062 mmol) in THF (5 mL) was placed under hydrogen (3 equiv., 2.70 mmol) pressure of 3 bar and the reaction was stirred for 18 h at 37° C. After this time, TLC indicated that the starting material has been consumed. The reaction mixture was filtered and the residue was washed with methanol. The organic layer was concentrated to give the title compound (0.216 g, 97% yield) which was used without further purification.

$^1$H NMR (400 MHz, CDCl$_3$): δ (ppm) 7.50-7.45 (m, 1H), 7.25-7.15 (m, 3H), 7.0 (s, 1 H), 5.35 (s, 2H), 3.40-3.10 (broad s, 2H), 2.42 (s, 3H), 2.30 (s, 3H).

Preparation of N'-(5-chloro-6-hydroxy-2-methyl-3-pyridyl)-N-ethyl-N-methyl-formamidine

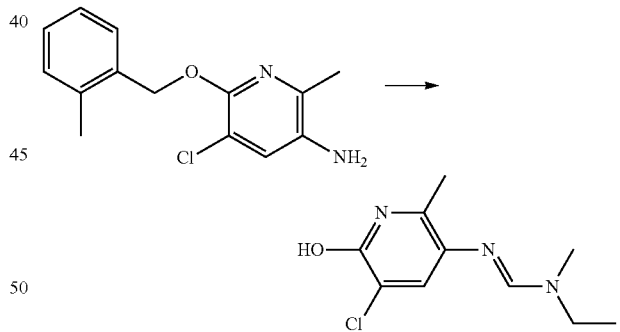

To a solution of N-ethyl-N-methyl-formamide (1.29 g, 14.76 mmol, 1.1 equiv) in dichloromethane (70 mL) was added phosphorus oxychloride (1.38 mL, 14.76 mmol, 1.1 equiv). The solution was stirred for 1.5 h at room temperature and then a solution of 5-chloro-2-methyl-6-(o-tolyl-methoxy)pyridin-3-amine (3.52 g, 13.41 mmol) in dichloromethane (10 mL) was added dropwise. After being stirred for 20 h at room temperature the solid was filtered and washed with dichloromethane. The residue was purified by combiflash column chromatography (silica gel, dichloromethane/methanol+5% triethylamine v/v=10/0 to 9/1). Fractions containing the compound were collected and concentrated in vacuo to give the title compound (2.52 g, 82% yield) as a yellow solid.

¹H NMR (400 MHz, CD₃OD): δ (ppm) 7.65-7.50 (broad s, 1 H), 3.50-3.30 (broad s, 1 H), 3.0 (s, 2H), 2.25 (s, 3H), 1.35 (m, 3H), 1.25 (m, 3H).

Preparation of N'-[5-chloro-2-methyl-6-(1-methyl-2-propoxy-ethoxy)-3-pyridyl]-N-ethyl-N-methyl-formamidine

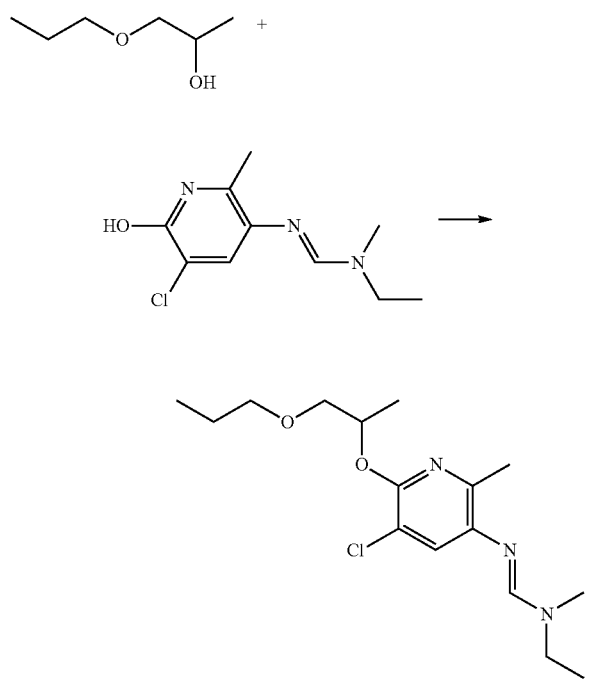

To a stirred solution of N'-(5-chloro-6-hydroxy-2-methyl-3-pyridyl)-N-ethyl-N-methyl-formamidine (0.25 g, 1.10 mmol) in THF (10 mL), 1-propoxypropan-2-ol (0.14 g, 1.21 mmol, 1.1 equiv) and triphenylphosphine (0.32 g, 1.21 mmol, 1.1 equiv) were added at room temperature under inert atmosphere (Ar). To this mixture, DIAD (diisopropyl diazodicarboxylate) (0.24 mL, 1.21 mmol, 1.1 equiv) was added dropwise over 10 minutes while keeping the temperature below 40° C. The reaction mixture was stirred for 16 h under heating at 60° C. After this time, triphenylphosphine (0.15 g, 0.55 mmol, 0.5 equiv) and DIAD (diisopropyl diazodicarboxylate) (0.11 mL, 0.55 mmol, 0.5 equiv) were added again and the reaction mixture was further stirred for 9 h. The reaction mixture was allowed to reach room temperature before quenching with water (10 mL) and 2M NaOH aqueous solution (2 mL). The water phase was extracted with ethyl acetate (1×25 mL). The organic layers were combined, dried over anhydrous Na₂SO₄ and filtered. The solvent was removed in vacuo to give a brown residue, which was purified by combiflash column chromatography (silica gel, heptane/ethyl acetate, v/v=9/1 to 1/1). Fractions containing the pure compound were collected and concentrated in vacuo to give the title compound (0.19 g, 53% yield) as an yellow oil.

¹H NMR (400 MHz, CDCl₃): δ (ppm) 7.45-7.30 (broad s, 1 H), 7.05 (s, 1 H), 5.40-5.30 (m, 1 H), 3.70-3.60 (m, 1 H), 3.55-3.40 (m, 3H), 3.45-3.30 (broad m, 2H), 3.00 (s, 3H), 2.35 (s, 3H), 1.65-1.50 (m, 2H), 1.35 (m, 3H), 1.20 (m, 3H), 0.85 (t, 3H).

Preparation of 5-bromo-2-methyl-6-(1-methyl-2-propoxy-ethoxy)-3-nitro-pyridine

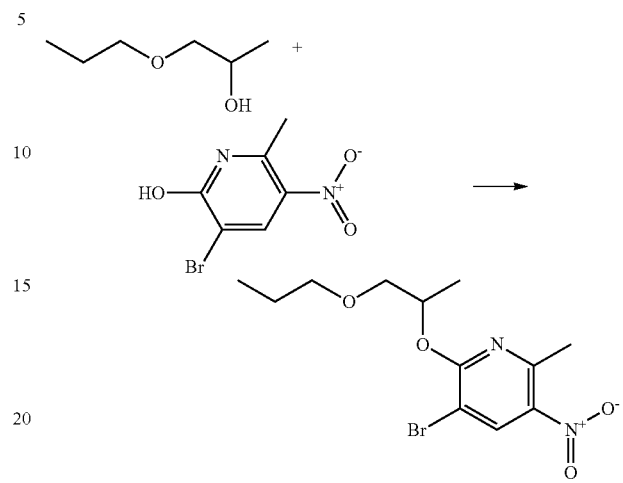

To a stirred suspension of 3-bromo-6-methyl-5-nitro-pyridin-2-ol (0.23 g, 1 mmol) in THF (0.08 mL), 1-propoxy-propan-2-ol (0.15 g, 1.2 mmol, 1.2 equiv) and triphenylphosphine (0.32 g, 1.2 mmol, 1.2 equiv) were added at room temperature under inert atmosphere (Ar). To this mixture, DIAD (diisopropyl diazodicarboxylate) (0.24 mL, 1.2 mmol, 1.2 equiv) was added dropwise over 10 minutes while keeping the temperature below 40° C. The reaction mixture was stirred for 12 h under heating at 65° C. After this time, LC-MS still showed remaining starting material but the reaction mixture was allowed to reach room temperature and the solvent was removed in vacuo to give a brown residue, which was purified by combiflash column chromatography (silica gel, heptane/triethylamine, v/v=95/5). Fractions containing the pure compound were collected and concentrated in vacuo to give the title compound (0.20 g, 60% yield) as a beige oil.

¹H NMR (400 MHz, CDCl₃): δ (ppm) 8.45 (s, 1 H), 5.50-5.40 (m, 1 H), 3.65-3.60 (m, 1H), 3.65-3.50 (m, 1H), 3.50-3.35 (m, 2H), 2.70 (s, 3H), 1.50 (m, 2H), 1.30 (m, 3H), 0.80 (t, 3H).

Preparation of 5-bromo-2-methyl-6-(1-methyl-2-propoxy-ethoxy)pyridin-3-amine

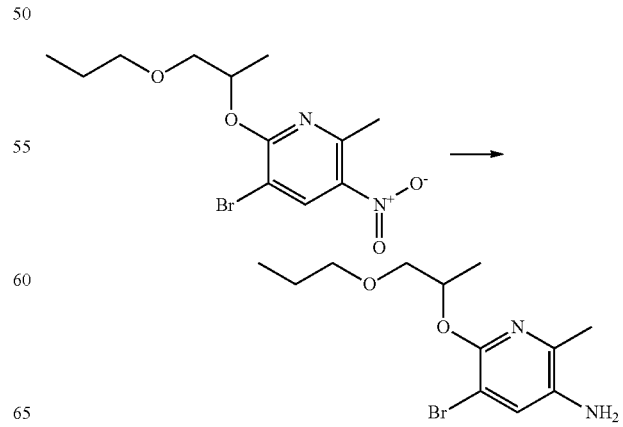

To a stirred suspension of 5-bromo-2-methyl-6-(1-methyl-2-propoxy-ethoxy)-3-nitro-pyridine (0.47 g, 1.41 mmol) in ethanol (10 mL) were added ammonium chloride (0.15 g, 2.82 mmol, 2 equiv), water (2.8 mL) and then iron (0.32 g, 5.64 mmol, 4 equiv). The reaction mixture was stirred for 4 h under heating at 85° C. As reaction monitoring still showed a lot of remaining starting material, ammonium chloride (0.75 g, 1.41 mmol, 1 equiv) and iron (0.16 g, 2.82 mmol, 2 equiv) were added and reaction mixture was further stirred for 10 h under heating at 85° C. After this time, LC-MS indicated that the starting material has been consumed and the reaction mixture was allowed to reach room temperature before filtering it over celite. The solvent was removed in vacuo and the residue was redissolved with ethyl acetate (15 mL). The organic phase was washed with a 2N aqueous NaOH solution (2×25 mL), dried over anhydrous $Na_2SO_4$ and filtered. The solvent was removed in vacuo to give a brown residue, which was purified by combiflash column chromatography (silica gel, heptane/ethyl acetate+10% triethylamine, v/v=10/0 to 1/1). Fractions containing the pure compound were collected and concentrated in vacuo to give the title compound (0.27 g, 63% yield) as an orange-brown oil.

$^1$H NMR (400 MHz, $CDCl_3$): δ (ppm) 7.10 (s, 1 H), 5.25-5.15 (m, 1H), 3.65-3.60 (m, 1 H), 3.55-3.50 (m, 3H), 3.50-3.35 (broad m, 2H), 2.20 (s, 3H), 1.50 (m, 2H), 1.25 (m, 3H), 0.80 (t, 3H).

Preparation of N'-[5-bromo-2-methyl-6-(1-methyl-2-propoxy-ethoxy)-3-pyridyl]-N-ethyl-formamidine

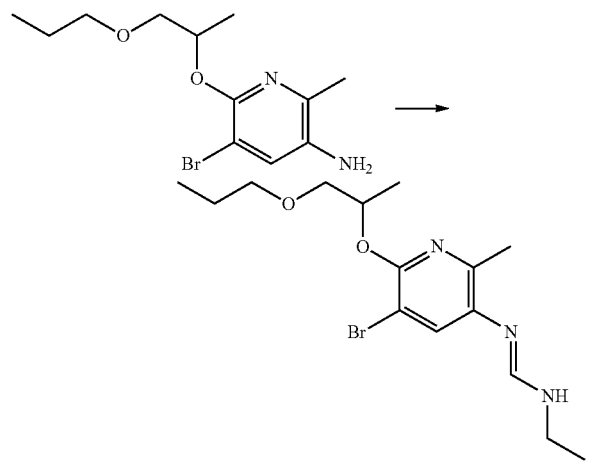

To a solution of N-ethylformamide (0.070 mL, 0.91 mmol, 1.1 equiv) in dichloromethane (6.6 mL) was added phosphorus oxychloride (0.085 mL, 0.91 mmol, 1.1 equiv). The solution was stirred for 1 h at room temperature. Then a solution of 5-bromo-2-methyl-6-(1-methyl-2-propoxy-ethoxy)pyridin-3-amine (0.25 g, 0.83 mmol) in dichloromethane (3 mL) was added dropwise. The suspension was stirred for 2 h at room temperature then poured onto a mixture of 2N aqueous NaOH solution (25 mL) and ice. The aqueous layer was separated, extracted with dichloromethane (2×15 mL). The organic phase was washed with 2N aqueous NaOH solution (25 mL) and brine (25 mL), dried over anhydrous $Na_2SO_4$ and filtered. The solvent was removed in vacuo to give a dark yellow residue, which was purified by reverse phase preparative HPLC to give the title compound (0.09 g, 29% yield) as an orange-brown oil.

$^1$H NMR (400 MHz, $CDCl_3$): δ (ppm) 7.45 (s, 1 H), 7.25 (s, 1 H), 5.40-5.30 (m, 1 H), 4.70-4.50 (broad s, 1 H), 3.75-3.60 (m, 1 H), 3.55-3.45 (m, 3H), 3.50-3.35 (broad m, 2H), 2.30 (s, 3H), 1.60-1.50 (m, 2H), 1.35 (m, 3H), 1.25 (m, 3H), 0.80 (t, 3H).

Preparation of N'-[5-bromo-2-methyl-6-(1-methyl-2-propoxy-ethoxy)-3-pyridyl]-N-methyl-formamidine

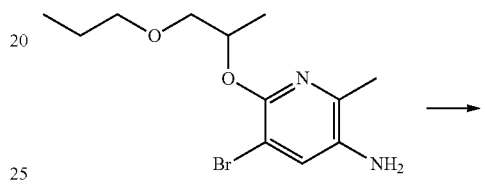

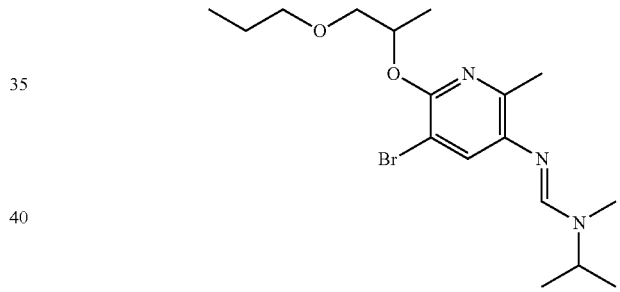

To a solution of N-methyl N-ethylformamide (0.30 g, 2.37 mmol, 1.1 equiv, 80% wt.) in dichloromethane (4.0 mL) was added phosphorus oxychloride (0.20 mL, 2.2 mmol, 1.1 equiv). The solution was stirred for 1 h at room temperature. Then a solution of 5-bromo-2-methyl-6-(1-methyl-2-propoxy-ethoxy)pyridin-3-amine (0.60 g, 2.0 mmol) in dichloromethane (0.5 mL) was added dropwise. The suspension was stirred for 2 h at room temperature. then poured onto a mixture of 2N aqueous NaOH solution (25 mL) and ice. The aqueous layer was separated, extracted with dichloromethane (2×15 mL). The organic phase was washed with 2N aqueous NaOH solution (25 mL) and brine (25 mL), dried over anhydrous $Na_2SO_4$ and filtered. The solvent was removed in vacuo to give a dark yellow residue, which was purified by reverse phase preparative HPLC to give the title compound (0.30 g, 40% yield) as an orange oil.

$^1$H NMR (400 MHz, $CDCl_3$): δ (ppm) 7.47 (broad s, 1 H), 7.25 (s, 1 H), 5.40-5.30 (m, 2H), 3.70-3.64 (m, 3H), 3.60-3.40 (m, 3H), 2.94 (broad s, 2H) 2.35 (d, 3H), 1.65-1.50 (m, 2H), 1.35 (m, 3H), 1.25 (m, 6H), 0.90 (t, 3H).

TABLE 67

This table gives analytical data for compounds of formula (I) prepared using techniques analogous to those above, as well as those described in WO 12/146125 (pp.370-378) and further techniques known to the person skilled in the art, for example as found in WO 08/101682 (pp.22-33).

| Compound No. | Structural formula | LC-Method: $R_t$ (min); MS-ESI (m/z; (M + H)$^+$); |
|---|---|---|
| 67.001 | 5-[(E)-[ethyl(methyl)amino]methyleneamino]-6-methyl-2-(1-methyl-2-propoxy-ethoxy)pyridine-3-carboxamide | Method 1 0.9 min.; 337 |
| 67.002 | N'-[5-bromo-2-methyl-6-[(1S)-1-methyl-2-propoxy-ethoxy]-3-pyridyl]-N-ethyl-N-methyl-formamidine | Method 1 0.76 min.; 372 |
| 67.003 | N'-[5-bromo-2-methyl-6-[(1R)-1-methyl-2-propoxy-ethoxy]-3-pyridyl]-N-ethyl-N-methyl-formamidine | Method 1 0.76 min.; 372 |
| 67.004 | 5-[(E)-[ethyl(methyl)amino]methyleneamino]-N,N,6-trimethyl-2-(1-methyl-2-propoxy-ethoxy)pyridine-3-carboxamide | Method 1 0.8 min.; 361 |
| 67.005 | 5-[(E)-[ethyl(methyl)amino]methyleneamino]-N,6-dimethyl-2-(1-methyl-2-propoxy-ethoxy)pyridine-3-carboxamide | Method 1 0.8 min.; 351 |
| 67.006 | 5-[(E)-[ethyl(methyl)amino]methyleneamino]-6-methyl-2-(1-methyl-2-propoxy-ethoxy)pyridine-3-carboxylic acid | Method 1 0.7 min.; 338 |
| 67.007 | N'-[5-cyano-2-methyl-6-(1-methyl-2-propoxy-ethoxy)-3-pyridyl]-N-ethyl-N-methyl-formamidine | Method 1 0.78 min.; 319 |
| 67.008 | N'-[5-bromo-2-methyl-6-(1-methyl-2-propoxy-ethoxy)-3-pyridyl]-N-isopropyl-N-methyl-formamidine | oil |
| 67.009 | N'-[5-(difluoromethyl)-2-methyl-6-(1-methyl-2-propoxy-ethoxy)-3-pyridyl]-N-ethyl-N-methyl-formamidine | Method 2 13.04 min.; 342 |
| 67.010 | N'-[5-(difluoromethoxy)-2-methyl-6-(1-methyl-2-propoxy-ethoxy)-3-pyridyl]-N-ethyl-N-methyl-formamidine | Method 1 0.85 min.; 360 |
| 67.011 | N'-[2,5-dimethyl-6-(1-methyl-2-propoxy-ethoxy)-3-pyridyl]-N-ethyl-N-methyl-formamidine | Method 1 0.79 min.; 308 |
| 67.012 | N-ethyl-N-methyl-N'-[2-methyl-6-(1-methyl-2-propoxy-ethoxy)-3-pyridyl]formamidine | Method 1 0.67 min.; 294 |
| 67.013 | N'-[5-bromo-2-methyl-6-(1-methyl-2-propoxy-ethoxy)-3-pyridyl]-N-ethyl-N-methyl-formamidine | Method 1 0.76 min.; 372 |
| 67.014 | N'-[6-(2-allyloxy-1-methyl-ethoxy)-5-chloro-2-methyl-3-pyridyl]-N-ethyl-N-methyl-formamidine | Method 3 1.08 min.; 326 |
| 67.015 | N'-[5-chloro-2-methyl-6-(1-methyl-2-propoxy-ethoxy)-3-pyridyl]-N-ethyl-N-methyl-formamidine | Method 1 1.11 min.; 328 |
| 67.016 | N'-[6-[1-(allyloxymethyl)-2-methoxy-ethoxy]-5-bromo-2-methyl-3-pyridyl]-N-ethyl-N-methyl-formamidine | Method 3 1.02 min.; 400 |
| 67.017 | N'-[6-(2-allyloxy-1-methyl-ethoxy)-5-cyano-2-methyl-3-pyridyl]-N-ethyl-N-methyl-formamidine | Method 3 0.96 min.; 317 |
| 67.018 | N'-[5-bromo-2-methyl-6-(1-methyl-2-propoxy-ethoxy)-3-pyridyl]-N-isopropyl-N-methyl-formamidine | oil |
| 67.019 | Methyl 5-[(E)-[ethyl(methyl)amino]methyleneamino]-6-methyl-2-(1-methyl-2-propoxy-ethoxy)pyridine-3-carboxylate | Method 1 0.80 min.; 352 |
| 67.020 | N'-[5-cyano-2-methyl-6-[1-methyl-2-[3-(trifluoromethyl)phenoxy]ethoxy]-3-pyridyl]-N-ethyl-N-methyl-formamidine | Method 3 1.33 min.; 422 |
| 67.021 | N'-[6-[2-(4-chlorophenoxy)-1-methyl-ethoxy]-5-cyano-2-methyl-3-pyridyl]-N-ethyl-N-methyl-formamidine | Method 3 1.29 min.; 387 |
| 67.022 | N'-[5-cyano-2-methyl-6-(1-methyl-2-phenoxy-ethoxy)-3-pyridyl]-N-ethyl-N-methyl-formamidine | Method 3 1.21 min.; 353 |
| 67.023 | N'-[5-chloro-2-methyl-6-[1-methyl-2-[3-(trifluoromethyl)phenoxy]ethoxy]-3-pyridyl]-N-ethyl-N-methyl-formamidine | Method 3 1.38 min.; 430 |

TABLE 67-continued

This table gives analytical data for compounds of formula (I) prepared using techniques analogous to those above, as well as those described in WO 12/146125 (pp.370-378) and further techniques known to the person skilled in the art, for example as found in WO 08/101682 (pp.22-33).

| Compound No. | Structural formula | LC-Method: $R_t$ (min); MS-ESI (m/z; (M + H)$^+$); |
|---|---|---|
| 67.024 | N'-[5-chloro-6-[2-(4-chlorophenoxy)-1-methyl-ethoxy]-2-methyl-3-pyridyl]-N-ethyl-N-methyl-formamidine | Method 3 1.38 min.; 396 |
| 67.025 | N'-[5-chloro-2-methyl-6-(1-methyl-2-phenoxy-ethoxy)-3-pyridyl]-N-ethyl-N-methyl-formamidine | Method 3 1.23 min.; 362 |
| 67.026 | N'-[5-bromo-6-[2-(4-chlorophenoxy)-1-methyl-ethoxy]-2-methyl-3-pyridyl]-N-ethyl-N-methyl-formamidine | Method 3 1.37 min.; 440 |
| 67.027 | N'-[5-bromo-2-methyl-6-[1-methyl-2-[3-(trifluoromethyl)phenoxy]ethoxy]-3-pyridyl]-N-ethyl-N-methyl-formamidine | Method 3 1.42 min.; 474 |
| 67.028 | N'-[5-bromo-2-methyl-6-(1-methyl-2-phenoxy-ethoxy)-3-pyridyl]-N-ethyl-N-methyl-formamidine | Method 3 1.25 min.; 406 |
| 67.029 | N'-[5-bromo-2-methyl-6-(1-methyl-2-propoxy-ethoxy)-3-pyridyl]-N-cyclopropyl-N-methyl-formamidine | Method 1 0.77 min.; 371 |
| 67.030 | 1-(azetidin-1-yl)-N-[5-bromo-2-methyl-6-(1-methyl-2-propoxy-ethoxy)-3-pyridyl]methanimine | Method 1 0.76 min.; 385 |

Analytical Methods Used

Method 1: Mass spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 m, 30×2.1 mm, Temp: 60° C., DAD Wavelength range (nm): 210 to 500, Solvent Gradient: A=water+5% MeOH+0.05% HCOOH, B=Acetonitrile+0.05% HCOOH. Gradient: 0 min 0% B, 100% A; 1.2-1.5 min 100% B: Flow (ml/min) 0.85.

Method 2: Mass spectra were recorded on a Mass Spectrometer from Shimadzu (SQD or ZQ Single quadrupole mass spectrometer) equipped with an electrospray source (Polarity: positive or negative ions, Capillary: 1.5 kV, Cone range: unknown, Extractor: 5.00 V, Source Temperature: 200° C., Desolvation Temperature: 250° C., Cone Gas Flow: 90 L/Hr, Desolvation Gas Flow: 90 L/Hr, Mass range: 50 to 900 Da) and an SPD-20A from LC from Shimadzu: Solvent degasser, binary pump, heated column compartment and ultraviolet detector. Column: Diamonsil C18 (2) 5 u 150*4.6 mm, Temp: 40° C., SPD-20A Wavelength range (nm): 210 to 500, Solvent Gradient: A=water+0.1% F$_3$CCOOH, B=Acetonitrile+0.1% F$_3$CCOOH; Gradient: 0 min 10% B, 90% A; 15 min 100% B; Flow 1.00 (ml/min)

Method 3: Mass spectra were recorded on a ZQ2000 Mass Spectrometer from Waters (Single quadrupole mass spectrometer) equipped with an electrospray source (Polarity: positive ions, Capillary (kV) 3.5, Cone (V) 60.00, Extractor (V) 3.00, Source Temperature (° C.) 150, Desolvation Temperature (° C.) 350, Cone Gas Flow (L/Hr) 50, Desolvation Gas Flow (L/Hr) 800, Mass range: 140 to 800 Da) DAD Wavelength range (nm): 210 to 400, Type of column: Waters ACQUITY UPLC HSS T3; Column length: 30 mm; Internal diameter of column: 2.1 mm; Particle Size: 1.8 micron; Temperature: 60° C. Solvent Gradient: A=water+10% MeOH+0.1% HCOOH, B=Acetonitrile+0.1% HCOOH. Gradient: 0 min 0% B, 100% A; 2.5-2.8 min 100% B; 0% A; 3.0 min 100% A, 0% B: Flow (ml/min) 0.85.

Biological Examples

*Blumeria graminis* f. sp. *tritici* (*Erysiphe graminis* f. sp. *tritici*)/Wheat/Leaf Disc Preventative (Powdery Mildew on Wheat)

Wheat leaf segments cv. Kanzler were placed on agar in a multiwell plate (24-well format) and sprayed with the formulated test compound diluted in water. The leaf disks were inoculated by shaking powdery mildew infected plants above the test plates 1 day after application. The inoculated leaf disks were incubated at 20° C. and 60% rh under a light regime of 24 h darkness followed by 12 h light/12 h darkness in a climate chamber and the activity of a compound was assessed as percent disease control compared to untreated when an appropriate level of disease damage appears on untreated check leaf segments (6-8 days after application).

The following compounds gave at 200 ppm give at least 80% disease control in this test when compared to untreated control leaf disks under the same conditions, which show extensive disease development:
Q.002, Q.003, Q.007, Q.008, Q.009, Q.010, Q.011, Q.013, Q.014, Q.015, Q.016, Q.017, Q.018, Q.020, Q.021, Q.022, Q.023, Q.024, Q.025, Q.026, Q.027, Q.028, Q.029, Q.030.

*Puccinia recondita* f. sp. *tritici*/Wheat/Leaf Disc Preventative (Brown Rust)

Wheat leaf segments cv. Kanzler were placed on agar in multiwell plates (24-well format) and sprayed with the formulated test compound diluted in water. The leaf disks were inoculated with a spore suspension of the fungus 1 day after application. The inoculated leaf segments were incubated at 19° C. and 75% rh under a light regime of 12 h light/12 h darkness in a climate cabinet and the activity of a compound was assessed as percent disease control compared to untreated when an appropriate level of disease damage appears in untreated check leaf segments (7-9 days after application).

The following compounds gave at 200 ppm gave at least 80% disease control in this test when compared to untreated control leaf disks under the same conditions, which show extensive disease development:

Q.002, Q.003, Q.007, Q.008, Q.009, Q.010, Q.011, Q.013, Q.014, Q.015, Q.016, Q.017, Q.018, Q.020, Q.021, Q.022, Q.023, Q.024, Q.025, Q.026, Q.028, Q.029, Q.030

*Puccinia recondita* f. sp. *tritici*/Wheat/Leaf Disc Curative (Brown Rust)

Wheat leaf segments cv. Kanzler are placed on agar in multiwell plates (24-well format). The leaf segments are inoculated with a spore suspension of the fungus. Plates were stored in darkness at 19° C. and 75% rh. The formulated test compound diluted in water was applied 1 day after inoculation. The leaf segments were incubated at 19° C. and 75% rh under a light regime of 12 h light/12 h darkness in a climate cabinet and the activity of a compound was assessed as percent disease control compared to untreated when an appropriate level of disease damage appears in untreated check leaf segments (6-8 days after application).

The following compounds gave at 200 ppm gave at least 80% disease control in this test when compared to untreated control leaf disks under the same conditions, which show extensive disease development:

Q.002, Q.003, Q.007, Q.008, Q.009, Q.010, Q.011, Q.012, Q.013, Q.014, Q.015, Q.016, Q.017, Q.018, Q.019, Q.020, Q.021, Q.022, Q.023, Q.024, Q.025, Q.026, Q.027, Q.028, Q.029, Q.030.

*Phakopsora pachyrhizi* on Soybean, Preventive Treatment

The compound activity was tested under 1 day preventive conditions. Soybean plants with a fully enfolded first trifoliate leaf were sprayed with a track sprayer and 50 l/ha spray volume with the test compounds, either solo or in tankmix as shown in the table below. 1 day after application leaf discs were cut from the first trifoliate leaf and placed in multiwell plates on water-agar. 5 leaf discs per treatment where infested with spores of a triazole tolerant soybean rust strain. The multiwell plates where sealed and placed in an incubator 48 h in darkness and 12 h light/dark cycle afterwards. Rust infestation on leaf discs was evaluated visually 11 days after application and average activity calculated in relation to disease severity on untreated check leaf discs.

The following compounds gave at 200 ppm gave at least 80% disease control in this test when compared to untreated control leaf disks under the same conditions, which show extensive disease development:

Q.002, Q.003, Q.007, Q.008, Q.009, Q.010, Q.011, Q.012, Q.013, Q.014, Q.015, Q.016, Q.017, Q.018, Q.019 Q.020, Q.023, Q.024, Q.025, Q.026, Q.027, Q.028, Q.029, Q.030.

What is claimed is:

1. A compound, wherein said compound is selected from the group consisting of:
N'-[5-chloro-2-methyl-6-(1-methyl-2-propoxy-ethoxy)-3-pyridyl]-N-ethyl-N-methyl-formamidine
N'-[5-chloro-2-methyl-6-[1-methyl-2-[3-(trifluoromethyl)phenoxy]ethoxy]-3-pyridyl]-N-ethyl-N-methyl-formamidine;
N'-[5-chloro-6-(2-(4-chlorophenoxy)-1-methyl-ethoxy)-2-methyl-3-pyridyl]-N-ethyl-N-methyl-formamidine; and
N'-[5-chloro-2-methyl-6-(1-methyl-2-phenoxy-ethoxy)-3-pyridyl]-N-ethyl-N-methyl-formamidine.

2. The compound of claim 1, wherein the compound is N'-[5-chloro-2-methyl-6-(1-methyl-2-propoxy-ethoxy)-3-pyridyl]-N-ethyl-N-methyl-formamidine.

3. The compound of claim 1, wherein the compound is N'-[5-chloro-2-methyl-641-methyl-2-[3-(trifluoromethyl)phenoxy]ethoxy]-3-pyridyl]-N-ethyl-N-methyl-formamidine.

4. The compound of claim 1, wherein the compound is N'-[5-chloro-6-(2-(4-chlorophenoxy)-1-methyl-ethoxy)-2-methyl-3-pyridyl]-N-ethyl-N-methyl-formamidine.

5. The compound of claim 1, wherein the compound is N'-[5-chloro-2-methyl-6-(1-methyl-2-phenoxy-ethoxy)-3-pyridyl]-N-ethyl-N-methyl-formamidine.

6. A compound of formula (I):

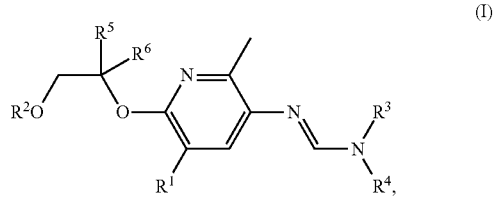

wherein
$R^1$ represents chlorine;
$R^2$ is n-propyl;
$R^3$ represents hydrogen or methyl;
$R^4$ is ethyl;
$R^5$ is hydrogen; and
$R^6$ is methyl.

* * * * *